(12) United States Patent
Yang et al.

(10) Patent No.: US 10,328,170 B2
(45) Date of Patent: Jun. 25, 2019

(54) DYNAMIC DISINFECTANT DOSAGE WITH CONCENTRATE DEGRADATION COMPENSATION

(71) Applicant: ETHICON, INC., Somerville, NJ (US)

(72) Inventors: Sungwook Yang, Los Angeles, CA (US); Cindy L. Ellis, Costa Mesa, CA (US); Robert P. Michaloski, Norwalk, CT (US); Marc Bellotti, Coto de Caza, CA (US); Yan Fang, Irvine, CA (US); Marco A. Mangiaterra, La Habra, CA (US)

(73) Assignee: Ethicon, Inc., Somerville, NJ (US)

( * ) Notice: Subject to any disclaimer, the term of this patent is extended or adjusted under 35 U.S.C. 154(b) by 232 days.

(21) Appl. No.: 15/331,133

(22) Filed: Oct. 21, 2016

(65) Prior Publication Data
US 2018/0110892 A1    Apr. 26, 2018

(51) Int. Cl.
*A61L 2/00* (2006.01)
*A61L 9/00* (2006.01)
(Continued)

(52) U.S. Cl.
CPC .................. *A61L 2/24* (2013.01); *A61B 1/12* (2013.01); *A61L 2/18* (2013.01); *A61L 2/183* (2013.01); *A61L 2/186* (2013.01); *A61L 2/26* (2013.01); *G01N 35/00* (2013.01); *A61L 2202/14* (2013.01); *A61L 2202/15* (2013.01); *A61L 2202/24* (2013.01)

(58) Field of Classification Search
CPC ... A61B 1/123; A61B 1/12; A61L 2/18; A61L 2/24; B08B 9/0325; B08B 3/10; B08B 3/102

USPC .... 422/1, 28, 32, 68.1, 119, 292; 134/33.13, 134/22.16, 22.19, 94.1, 109, 166 R; 600/133; 73/1.02
See application file for complete search history.

(56) References Cited

U.S. PATENT DOCUMENTS 6,068,815 A  *  5/2000  Oberleitner ............ A01N 37/16
                                                    134/170
6,986,736 B2    1/2006  Williams et al.
(Continued)

OTHER PUBLICATIONS

U.S. Appl. No. 15/157,952, filed May 18, 2016.

*Primary Examiner* — Monzer R Chorbaji
(74) *Attorney, Agent, or Firm* — Frost Brown Todd LLC

(57) ABSTRACT

A method for dynamic dosing of disinfectant solution in a medical device reprocessing system includes calculating a volume of an initial dose of concentrated disinfectant solution for dilution to make a first in-use disinfectant solution. The initial dose of concentrated disinfectant solution is diluted with diluting fluid to make the first in-use disinfectant solution comprising a target concentration of disinfectant agent. The first in-use disinfectant solution is applied to a medical device. A concentration of the disinfectant agent in the first in-use disinfectant solution is then calculated. The actual concentration of the disinfectant agent in the concentrated disinfectant solution is then calculated based upon the concentration of disinfectant agent in the first in-use disinfectant solution. It is then determined whether a volume of a second dose of concentrated disinfectant solution is increased or about the same as the volume of the initial dose to make a second in-use disinfectant solution.

19 Claims, 7 Drawing Sheets

(51) Int. Cl.
*G01D 11/26* (2006.01)
*A61B 1/00* (2006.01)
*B08B 9/00* (2006.01)
*G01N 21/00* (2006.01)
*A61L 2/24* (2006.01)
*A61L 2/18* (2006.01)
*A61B 1/12* (2006.01)
*A61L 2/26* (2006.01)
*G01N 35/00* (2006.01)

(56) References Cited

U.S. PATENT DOCUMENTS

| | | |
|---|---|---|
| 7,479,257 B2 | 1/2009 | Nguyen et al. |
| 7,686,761 B2 | 3/2010 | Jackson et al. |
| 7,879,289 B2 | 2/2011 | Williams |
| 8,246,909 B2 | 8/2012 | Williams et al. |
| 9,788,711 B2 | 10/2017 | Ogawa |
| 2016/0302654 A1 | 10/2016 | Ogawa |

* cited by examiner

DYNAMIC DISINFECTANT DOSAGE WITH CONCENTRATE DEGRADATION COMPENSATION

BACKGROUND

The below discussion relates to the reprocessing (e.g., decontamination, disinfection, high-level disinfection, and/or sterilization) of endoscopes and other instruments that are used in medical procedures. In particular, the below discussion relates to an apparatus and a method that may be used to reprocess a medical device such as an endoscope after the medical device has been used in a first medical procedure, such that the medical device may be safely used in a subsequent medical procedure. While the below discussion will speak mainly in terms of an endoscope, it should be understood that the discussion may also equally apply to certain other medical devices.

An endoscope may have one or more working channels or lumens extending along at least a portion of the length of the endoscope. Such channels may be configured to provide a pathway for passage of other medical devices, etc., into an anatomical region within a patient. These channels may be difficult to clean and/or disinfect using certain primitive cleaning and/or disinfecting techniques. Thus, the endoscope may be placed in a reprocessing system that is particularly configured to clean endoscopes, including the channels within endoscopes. Such an endoscope reprocessing system may wash and disinfect the endoscope. Such an endoscope reprocessing system may include a basin that is configured to receive the endoscope, with a pump that flows cleaning fluids over the exterior of the endoscope within the basin. The system may also include ports that couple with the working channels of the endoscope and associated pumps that flow cleaning fluids through the working channels of the endoscope. The process executed by such a dedicated endoscope reprocessing system may include a detergent washing cycle, followed by a rinsing cycle, followed by a sterilization or disinfection cycle, followed by another rinsing cycle. The sterilization or disinfection cycle may employ disinfectant solution and water rinses. The process may optionally include an alcohol flush to aid displacement of water. A rinsing cycle may be followed by an air flush for drying and storage.

Examples of systems and methods that may be used to reprocess a used endoscope are described in U.S. Pat. No. 6,986,736, entitled "Automated Endoscope Reprocessor Connection with Integrity Testing," issued Jan. 17, 2006, the disclosure of which is incorporated by reference herein; U.S. Pat. No. 7,479,257, entitled "Automated Endoscope Reprocessor Solution Testing," issued Jan. 20, 2009, the disclosure of which is incorporated by reference herein; U.S. Pat. No. 7,686,761, entitled "Method of Detecting Proper Connection of an Endoscope to an Endoscope Reprocessor," issued Mar. 30, 2010, the disclosure of which is incorporated by reference herein; and U.S. Pat. No. 8,246,909, entitled "Automated Endoscope Reprocessor Germicide Concentration Monitoring System and Method," issued Aug. 21, 2012, the disclosure of which is incorporated by reference herein. An example of a commercially available endoscope reprocessing system is the EVOTECH® Endoscope Cleaner and Reprocessor (ECR) by Advanced Sterilization Products of Irvine, Calif.

For the disinfection cycle of a reprocessing system to be effective, it may be important to ensure that the disinfectant solution is sufficiently concentrated. Conventionally, disinfectant solutions may be sold as concentrated disinfectant stock solution, hereinafter, "concentrated stock solution." While utilizing concentrated stock solution in an endoscope reprocessing system may provide for effective disinfection of an endoscope, the relatively high concentration of active ingredients in the concentrated stock solution may be unnecessarily harsh to, or incompatible with, various components of the endoscope. Thus, to decrease unnecessary wear and tear on an endoscope while still providing for a minimum effective concentration of disinfectant agent, an aliquot of concentrated stock solution may be diluted to an appropriate usage concentration before being employed in a disinfection cycle of an endoscope reprocessing system. Once the diluted disinfectant solution is used in a disinfection cycle, it may be discarded, and a new dose of concentrated stock solution diluted for use in a subsequent disinfection cycle.

Concentrated stock solution may be dosed out for usage in an endoscope reprocessing system over a protracted period of time, such as over the course of several hours, days, weeks, or even months. Consequently, disinfectant agent in the concentrated stock solution may become unstable and/or degrade, thereby reducing the potency of the concentrated stock solution. To compensate for the reduced potency, the known shelf-life of a disinfectant reagent may be utilized to estimate the concentration of disinfectant agent in a concentrated stock solution at any given time. Based upon the estimation, dilution of the concentrated stock solution may be decreased in an attempt to ensure that at least a minimum effective concentration of disinfectant agent is present in the disinfectant solution for use in a subsequent disinfection cycle.

Reliance upon assumptions of disinfectant agent concentration in a concentrated stock solution may result in a number of significant problems. For example, an endoscope to be disinfected may be inadvertently exposed to unnecessarily high concentrations of disinfectant agent, which may in turn shorten the useful life of the endoscope and/or components thereof. In addition, an errant assumption of disinfectant agent concentration may result in under-dilution of concentrated stock solution, which may in turn result in costly waste.

While a variety of systems and methods have been made and used to reprocess medical devices, it is believed that no one prior to the inventor(s) has made or used the technology as described herein.

BRIEF DESCRIPTION OF THE DRAWINGS

It is believed the present invention will be better understood from the following description of certain examples taken in conjunction with the accompanying drawings, in which like reference numerals identify the same elements and in which.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Medical Device Reprocessing Apparatus

Figure 1:
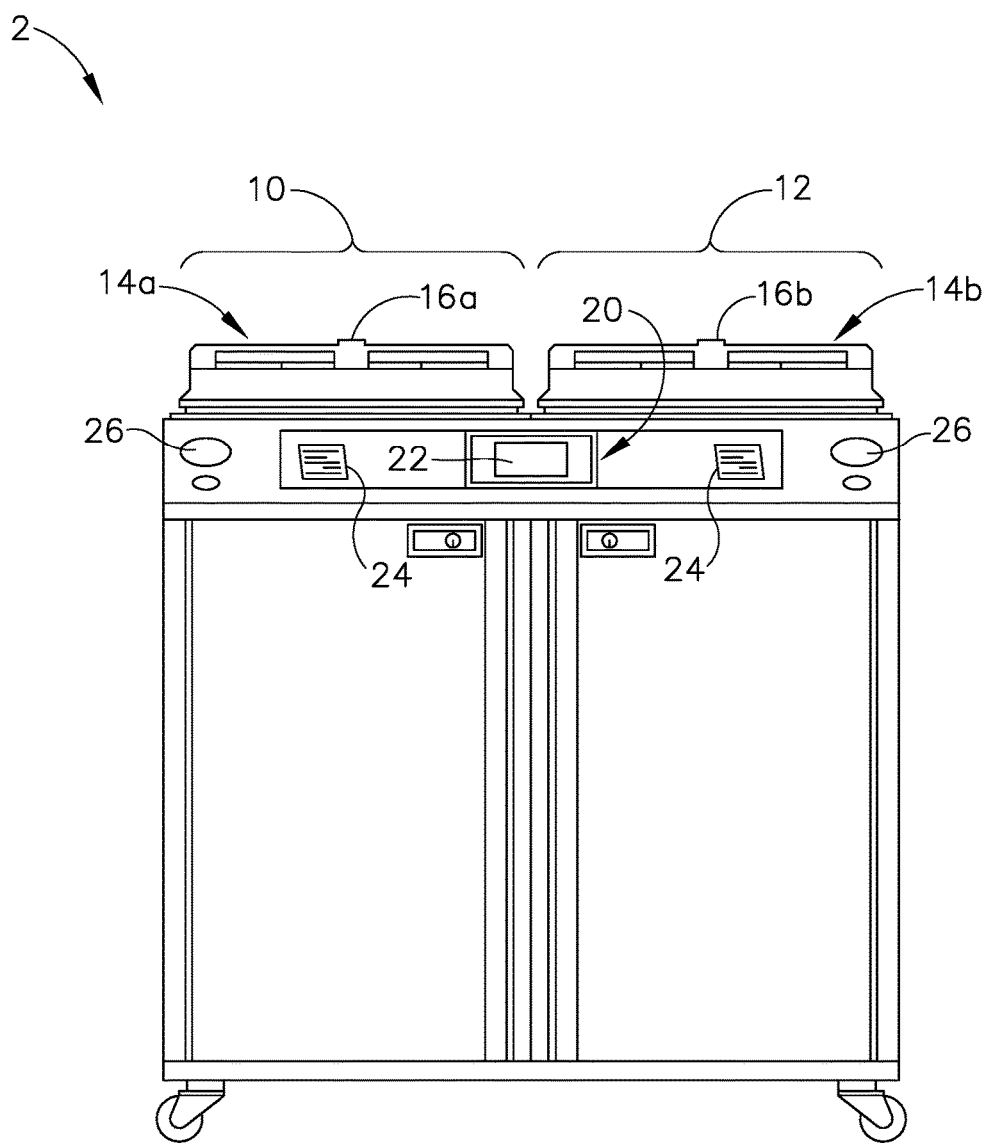
FIG. 1 depicts a front elevational view of an exemplary reprocessing system.
Figure 2:
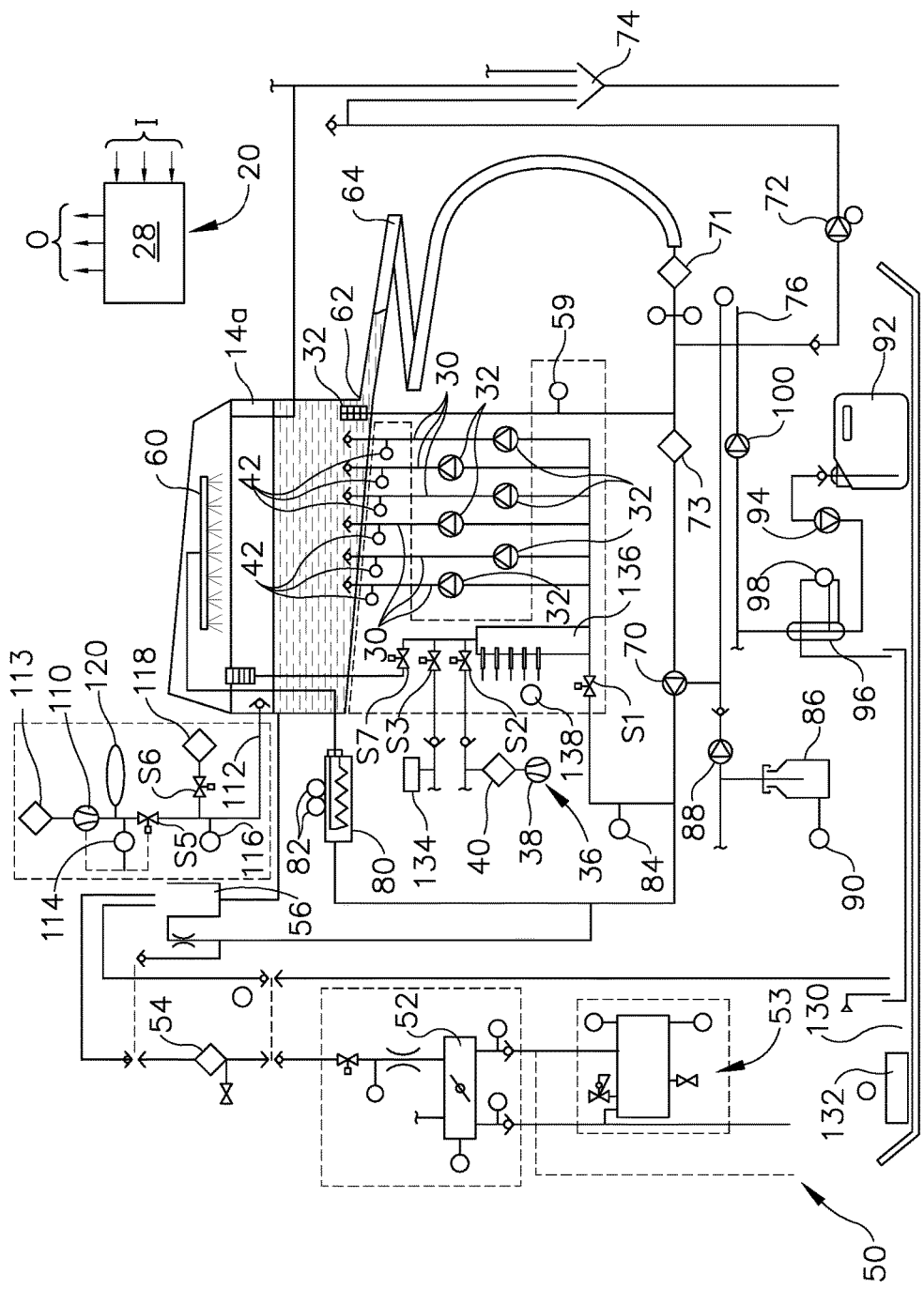
FIG. 2 depicts a schematic diagram of the reprocessing system of FIG. 1, with only a single decontamination basin shown for clarity.

FIGS. 1-2 show an exemplary reprocessing system (2) that may be used to decontaminate endoscopes and other medical devices that include channels or lumens formed therethrough. System (2) of this example generally includes a first station (10) and a second station (12). Stations (10, 12) are at least substantially similar in all respects to provide for the decontamination of two different medical devices simultaneously or in series. First and second decontamination basins (14a, 14b) receive the contaminated devices. Each basin (14a, 14b) is selectively sealed by a respective lid (16a, 16b). In the present example, lids (16a, 16b) cooperate with respective basins (14a, 14b) to provide a microbe-blocking relationship to prevent the entrance of environmental microbes into basins (14a, 14b) during decontamination operations. By way of example only, lids (16a, 16b) may include a microbe removal or HEPA air filter formed therein for venting.

A control system (20) includes one or more microcontrollers, such as a programmable logic controller (PLC), for controlling decontamination and user interface operations. Although one control system (20) is shown herein as controlling both decontamination stations (10, 12), those skilled in the art will recognize that each station (10, 12) can include a dedicated control system. A visual display (22) displays decontamination parameters and machine conditions for an operator, and at least one printer (24) prints a hard copy output of the decontamination parameters for a record to be filed or attached to the decontaminated device or its storage packaging. It should be understood that printer (24) is merely optional. In some versions, visual display (22) is combined with a touch screen input device. In addition, or in the alternative, a keypad and/or other user input feature is provided for input of decontamination process parameters and for machine control. Other visual gauges (26) such as pressure meters and the like provide digital or analog output of decontamination or medical device leak testing data.

FIG. 2 diagrammatically illustrates just one decontamination station (10) of reprocessing system (2), but those skilled in the art will recognize that decontamination station (12) may be configured and operable just like decontamination station (10). It should also be understood that reprocessing system (2) may be provided with just one single decontamination station (10, 12) or more than two decontamination stations (10, 12).

Decontamination basin (14a) receives an endoscope (200) (see FIG. 3) or other medical device therein for decontamination. While basin (14a) is described herein as receiving just one endoscope (200) in the present example, it should be understood that some versions may be configured to receive two or more endoscopes (200) in basin (14a). Any internal channels of endoscope (200) are connected with flush conduits, such as flush lines (30). Each flush line (30) is connected to an outlet of a corresponding pump (32), such that each flush line (30) has a dedicated pump (32) in this example. Pumps (32) of the present example comprise peristaltic pumps that pump fluid, such as liquid and air, through the flush lines (30) and any internal channels of endoscope (200). Alternatively, any other suitable kind of pump(s) may be used. In the present example, pumps (32) can either draw liquid from basin (14a) through a filtered drain and a valve (S1); or draw decontaminated air from an air supply system (36) through a valve (S2). Air supply system (36) of the present example includes a pump (38) and a microbe removal air filter (40) that filters microbes from an incoming air stream.

A pressure switch or sensor (42) is in fluid communication with each flush line (30) for sensing excessive pressure in the flush line. Any excessive pressure or lack of flow sensed may be indicative of a partial or complete blockage (e.g., by bodily tissue or dried bodily fluids) in an endoscope (200) channel to which the relevant flush line (30) is connected. The isolation of each flush line (30) relative to the other flush lines (30) allows the particular blocked channel to be easily identified and isolated, depending upon which sensor (42) senses excessive pressure or lack of flow. In some other versions, flush lines (30) are not isolated relative to each other.

Basin (14a) is in fluid communication with a water source (50), such as a utility or tap water connection including hot and cold inlets, and a mixing valve (52) flowing into a break tank (56). A microbe removal filter (54), such as a 0.2 μm or smaller absolute pore size filter, decontaminates the incoming water, which is delivered into break tank (56) through the air gap to prevent backflow. A sensor (59) monitors liquid levels within basin (14a). An optional water heater (53) can be provided if an appropriate source of hot water is not available. The condition of filter (54) can be monitored by directly monitoring the flow rate of water therethrough or indirectly by monitoring the basin fill time using a float switch or the like. When the flow rate drops below a select threshold, this indicates a partially clogged filter element that requires replacement.

A basin drain (62) drains liquid from basin (14a) through an enlarged helical tube (64) into which elongated portions of endoscope (200) can be inserted. Drain (62) is in fluid communication with a recirculation pump (70) and a drain pump (72). Recirculation pump (70) recirculates liquid from basin drain (62) to a spray nozzle assembly (60), which sprays the liquid into basin (14a) and onto endoscope (200). A coarse screen (71) and a fine screen (73) filter out particles in the recirculating fluid. Drain pump (72) pumps liquid from basin drain (62) to a utility drain (74). A level sensor (76) monitors the flow of liquid from pump (72) to utility drain (74). Pumps (70, 72) can be simultaneously operated such that liquid is sprayed into basin (14a) while basin (14a) is being drained, to encourage the flow of residue out of basin (14a) and off of endoscope (200). Of course, a single pump and a valve assembly could replace dual pumps (70, 72).

An inline heater (80), with temperature sensors (82), upstream of recirculation pump (70), heats the liquid to optimum temperatures for cleaning and/or disinfection. A pressure switch or sensor (84) measures pressure downstream of circulation pump (70). In some variations, a flow sensor is used instead of pressure sensor (84), to measure fluid flow downstream of circulation pump (70). Detergent solution (86) is metered into the flow downstream of circulation pump (70) via a metering pump (88). A float switch (90) indicates the level of detergent (86) available. Disinfectant in the form of a concentrated stock solution (92) is metered into the flow upstream of circulation pump (70) via a metering pump (94). To more accurately meter concentrated stock solution (92), pump (94) fills a metering prechamber (96) under control of a fluid level switch (98) and control system (20). By way of example only, concentrated stock solution (92) may comprise CIDEX© Activated Glutaraldehyde Solution by Advanced Sterilization Products of Irvine, Calif. By way of further example only, concentrated stock solution (92) may comprise ortho-phthalaldehyde (OPA). By way of further example only, concentrated stock solution (92) may comprise peracetic acid (PAA). By way of further example only, concentrated stock solution (92) may comprise peracetic acid, ortho-phthalaldehyde (OPA), glutaraldehyde, peroxide, ozone, and/or combinations thereof, or any other possible disinfectants or combinations so long as they are susceptible to measurement and adjustment of their concentration in an in-use disinfectant solution.

Some endoscopes (200) include a flexible outer housing or sheath surrounding the individual tubular members and the like that form the interior channels and other parts of endoscope (200). This housing defines a closed interior space, which is isolated from patient tissues and fluids during medical procedures. It may be important that the sheath be maintained intact, without cuts or other holes that would allow contamination of the interior space beneath the sheath. Therefore, reprocessing system (2) of the present example includes means for testing the integrity of such a sheath. In particular, an air pump (e.g., pump (38) or another pump (110)) pressurizes the interior space defined by the sheath of endoscope (200) through a conduit (112) and a valve (S5). In the present example, a HEPA or other microbe-removing filter (113) removes microbes from the pressurizing air. A pressure regulator (114) prevents accidental over pressurization of the sheath. Upon full pressurization, valve (S5) is closed and a pressure sensor (116) looks for a drop in pressure in conduit (112), which would indicate the escape of air through the sheath of endoscope (200). A valve (S6) selectively vents conduit (112) and the sheath of endoscope (200) through an optional filter (118) when the testing procedure is complete. An air buffer (120) smooths out pulsation of pressure from air pump (110).

In the present example, each station (10, 12) also contains a drip basin (130) and spill sensor (132) to alert the operator to potential leaks.

An alcohol supply (134), controlled by a valve (S3), can supply alcohol to channel pumps (32) after rinsing steps, to assist in removing water from channels (210, 212, 213, 214, 217, 218) of endoscope (200).

Flow rates in lines (30) can be monitored via channel pumps (32) and pressure sensors (42). If one of pressure sensors (42) detects too high a pressure, the associated pump (32) is deactivated. The flow rate of pump (32) and its activated duration time provide a reasonable indication of the flow rate in an associated line (30). These flow rates are monitored during the process to check for blockages in any of the channels of endoscope (200). Alternatively, the decay in the pressure from the time pump (32) cycles off can also be used to estimate the flow rate, with faster decay rates being associated with higher flow rates.

A more accurate measurement of flow rate in an individual channel may be desirable to detect subtler blockages. To that end, a metering tube (136) having a plurality of level indicating sensors (138) fluidly connects to the inputs of channel pumps (32). In some versions, a reference connection is provided at a low point in metering tube (136) and a plurality of sensors (138) are arranged vertically above the reference connection. By passing a current from the reference point through the fluid to sensors (138), it can be determined which sensors (138) are immersed and therefore determine the level within metering tube (136). In addition, or in the alternative, any other suitable components and techniques may be used to sense fluid levels. By shutting valve (S1) and opening a vent valve (S7), channel pumps (32) draw exclusively from metering tube (136). The amount of fluid being drawn can be very accurately determined based upon sensors (138). By running each channel pump (32) in isolation, the flow therethrough can be accurately determined based upon the time and the volume of fluid emptied from metering tube (136).

In addition to the input and output devices described above, all of the electrical and electromechanical devices shown are operatively connected to and controlled by control system (20). Specifically, and without limitation, switches and sensors (42, 59, 76, 84, 90, 98, 114, 116, 132 136) provide input (I) to microcontroller (28), which controls the cleaning and/or disinfection cycles and other machine operations in accordance therewith. For example, microcontroller (28) includes outputs (O) that are operatively connected to pumps (32, 38, 70, 72, 88, 94, 100, 110), valves (S1, S2, S3, S5, S6, S7), and heater (80) to control these devices for effective cleaning and/or disinfection cycles and other operations.

Figure 3:
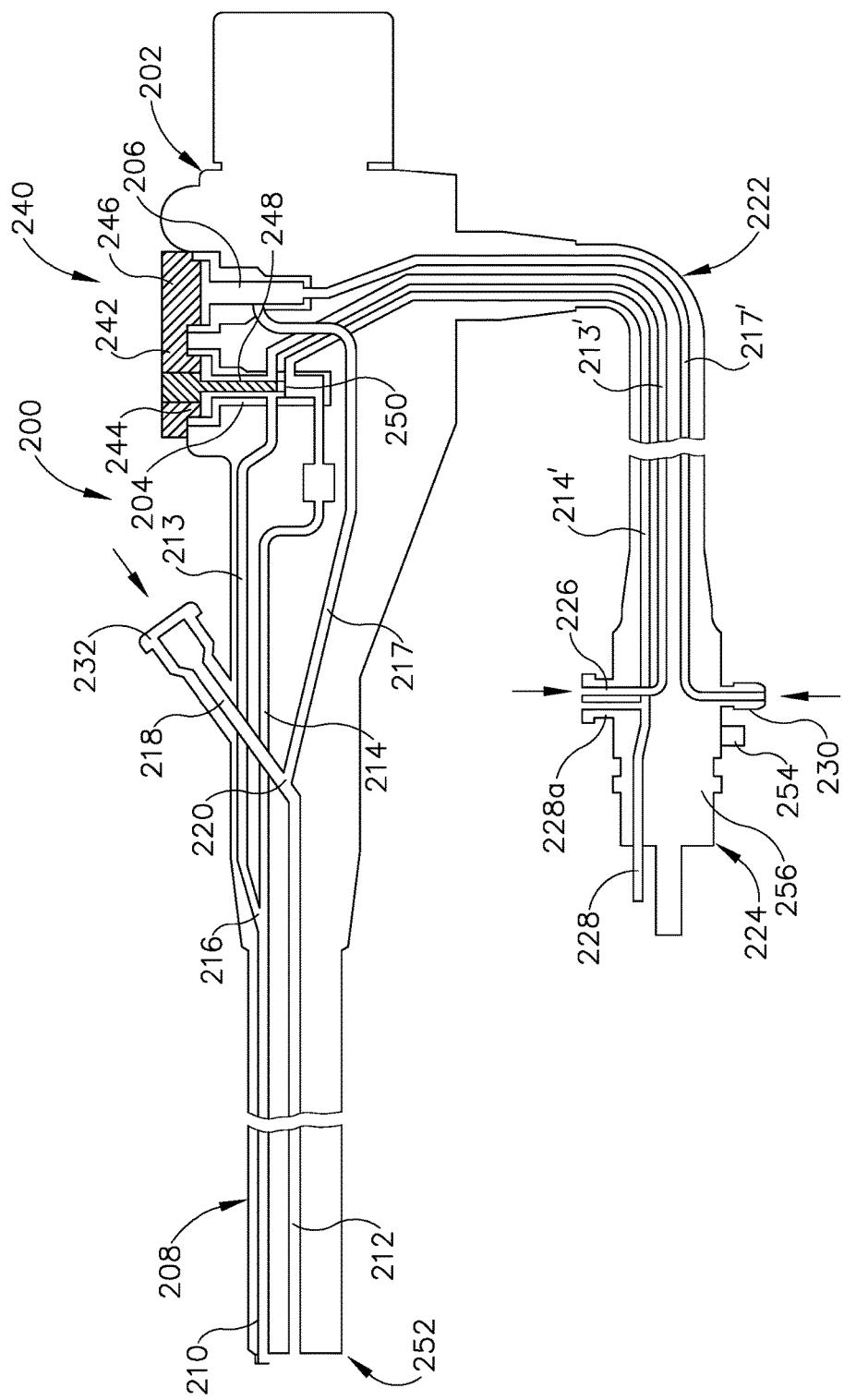
FIG. 3 depicts a cross-sectional side view of proximal and distal portions of an endoscope that may be decontaminated using the reprocessing system of FIG. 1.

As shown in FIG. 3, endoscope (200) has a head part (202). Head part (202) includes openings (204, 206) formed therein. During normal use of endoscope (200), an air/water valve (not shown) and a suction valve (not shown) are arranged in openings (204, 206). A flexible shaft (208) is attached to head part (202). A combined air/water channel (210) and a combined suction/biopsy channel (212) are accommodated in shaft (208). A separate air channel (213) and water channel (214) are also arranged in head part (202) and merge into air/water channel (210) at the location of a joining point (216). It will be appreciated that the term "joining point" as used herein refers to an intersecting junction rather than being limited to a geometrical point and, the terms may be used interchangeably. Furthermore, a separate suction channel (217) and biopsy channel (218) are accommodated in head part (202) and merge into suction/biopsy channel (212) at the location of a joining point (220).

In head part (202), air channel (213) and water channel (214) open into opening (204) for the air/water valve (not shown). Suction channel (217) opens into opening (206) for the suction valve (not shown). Furthermore, a flexible feed hose (222) connects to head part (202) and accommodates channels (213', 214', 217'), which are connected to air channel (213), water channel (214), and suction channel (217) via respective openings (204, 206). In practice, feed hose (222) may also be referred to as the light-conductor casing. The mutually connecting air channels (213, 213') will collectively be referred to below as air channel (213). The mutually connecting water channels (214, 214') will collectively be referred to below as water channel (214). The mutually connecting suction channels (217, 217') will collectively be referred to below as suction channel (217). A connection (226) for air channel (213), connections (228, 228a) for water channel (214), and a connection (230) for suction channel (217) are arranged on the end section (224) (also referred to as the light conductor connector) of flexible hose (222). When the connection (226) is in use, connection (228a) is closed off. A connection (232) for biopsy channel (218) is arranged on head part (202).

A channel separator (240) is shown inserted into openings (204, 206). Channel separator (240) comprises a body (242) and plug members (244, 246), which occlude respective openings (204, 206). A coaxial insert (248) on plug member (244) extends inwardly of opening (204) and terminates in an annular flange (250), which occludes a portion of opening (204) to separate channel (213) from channel (214). By connecting lines (30) to openings (226, 228, 228a, 230, 232), liquid for cleaning and disinfection can be flowed through endoscope channels (213, 214, 217, 218) and out of a distal tip (252) of endoscope (200) via channels (210, 212). Channel separator (240) ensures that such liquid flows all the way through endoscope (200) without leaking out of openings (204, 206); and isolates channels (213, 214) from each other so that each channel (213, 214) has its own independent flow path. One of skill in the art will appreciate that various endoscopes having differing arrangements of channels and openings may require modifications to channel separator (240) to accommodate such differences while occluding ports in head (202) and keeping channels separated from each other so that each channel can be flushed independently of the other channels. Otherwise, a blockage in one channel might merely redirect flow to a connected unblocked channel.

A leakage port (254) on end section (224) leads into an interior portion (256) of endoscope (200) and is used to check for the physical integrity thereof, namely to ensure that no leakage has formed between any of the channels and the interior (256) or from the exterior to the interior (256).

II. Exemplary Medical Device Reprocessing Method

In an exemplary use of reprocessing system (2), an operator may start by actuating a foot pedal (not shown) to open basin lid (16a). Each lid (16a, 16b) may have its own foot pedal. In some versions, once pressure is removed from the foot pedal, the motion of lid (16a, 16b) stops. With lid (16a) open, the operator inserts shaft (208) of endoscope (200) into helical circulation tube (64). End section (224) and head section (202) of endoscope (200) are situated within basin (14a), with feed hose (222) coiled within basin (14a) with as wide a diameter as possible. Next, flush lines (30) are attached to respective endoscope openings (226, 228, 228a, 230, 232). Air line (112) is also connected to connector (254). In some versions, flush lines (30) are color coded, and guide located on station (10) provides a reference for the color-coded connections.

Depending on the customer-selectable configuration, control system (20) may prompt the operator to enter a user code, patient ID, endoscope code, and/or specialist code. This information may be entered manually (e.g., through touch screen (22)), automatically (e.g., by using an attached barcode wand), or in any other suitable fashion. With the information entered (if required), the operator may then close lid (16a). In some versions, closing lid (16a) requires the operator to press a hardware button and a touch-screen (22) button simultaneously to provide a fail-safe mechanism for preventing the operator's hands from being caught or pinched by the closing basin lid (16a). If either the hardware button or software button is released while lid (16a) is in the process of closing, the motion of lid (16a) stops.

Once lid (16a) is closed, the operator presses a button on touch-screen (22) to begin the washing/disinfection process. At the start of the washing/disinfection process, air pump (38) is activated and pressure within the body of endoscope (200) is monitored. When pressure reaches a predetermined level (e.g., 250 mbar), pump (38) is deactivated, and the pressure is allowed to stabilize for a certain stabilization period (e.g., 6 seconds). If pressure has not reached a certain pressure (e.g., 250 mbar) in a certain time period (e.g., 45 seconds), the program is stopped and the operator is notified of a leak. If pressure drops below a threshold (e.g., less than 100 mbar) during the stabilization period, the program is stopped and the operator is notified of the condition. Once the pressure has stabilized, the pressure drop is monitored over the course of a certain duration (e.g., 60 seconds). If pressure drop is faster than a predetermined rate (e.g., more than 10 mbar within 60 seconds), the program is stopped and the operator is notified of the condition. If the pressure drop is slower than a predetermined rate (e.g., less than 10 mbar in 60 seconds), reprocessing system (2) continues with the next step. A slight positive pressure is held within the body of endoscope (200) during the rest of the process to prevent fluids from leaking in.

A second leak test checks the adequacy of connection to the various ports (226, 228, 228a, 230, 232) and the proper placement of channel separator (240). A quantity of water is admitted to basin (14a) so as to submerge the distal end of endoscope (200) in helical tube (64). Valve (S1) is closed and valve (S7) opened; and pumps (32) are run in reverse to draw a vacuum and to ultimately draw liquid into endoscope channels (210, 212). Pressure sensors (42) are monitored to make sure that the pressure in any one channel (210, 212) does not drop and/or raise by more than a predetermined amount in a given time frame. If it does, it likely indicates that one of the connections was not made correctly and air is leaking into channel (210, 212). In any event, in the presence of an unacceptable pressure drop, control system (20) will cancel the cycle and indicate a likely faulty connection, preferably with an indication of which channel (210, 212) failed.

In the event that the leak tests are passed, reprocessing system (2) continues with a pre-rinse cycle. The purpose of this step is to flush water through channels (210, 212, 213, 214, 217, 218) to remove waste material prior to washing and disinfecting endoscope (200). To initiate the pre-rinse cycle, basin (14a) is filled with filtered water and the water level is detected by pressure sensor (59) below basin (14a). The water is pumped via pumps (32) through the interior of channels (210, 212, 213, 214, 217, 218), directly to drain (74). This water is not recirculated around the exterior surfaces of endoscope 200 during this stage. As the water is being pumped through channels (210, 212, 213, 214, 217, 218), drain pump (72) is activated to ensure that basin (14a) is also emptied. Drain pump (72) will be turned off when drain switch (76) detects that the drain process is complete. During the draining process, sterile air is blown via air pump (38) through all endoscope channels (210, 212, 213, 214, 217, 218) simultaneously, to minimize potential carryover.

Once the pre-rinse cycle is complete, reprocessing system (2) continues with a wash cycle. To begin the wash cycle, basin (14a) is filled with warm water (e.g., approximately 35° C.). Water temperature is controlled by controlling the mix of heated and unheated water. The water level is detected by pressure sensor (59). Reprocessing system (2) then adds enzymatic detergent to the water circulating in reprocessing system (2) by means of peristaltic metering pump (88). The volume is controlled by controlling the delivery time, pump speed, and inner diameter of the tubing of pump (88). Detergent solution (86) is actively pumped throughout the internal endoscope channels (210, 212, 213, 214, 217, 218) and over the outer surface of endoscope (200) for a predetermined time period (e.g., from one to five minutes, or more particularly about three minutes), by channel pumps (32) and external circulation pump (70). Inline heater (80) keeps the temperature at a predetermined temperature (e.g., approximately about 35° C.).

After detergent solution (86) has been circulating for a certain period of time (e.g., a couple of minutes), the flow rate through channels (210, 212, 213, 214, 217, 218) is measured. If the flow rate through any channel (210, 212, 213, 214, 217, 218) is less than a predetermined rate for that channel (210, 212, 213, 214, 217, 218), the channel (210, 212, 213, 214, 217, 218) is identified as blocked, the program is stopped, and the operator is notified of the condition. Peristaltic pumps (32) are run at their predetermined flow rates and cycle off in the presence of unacceptably high pressure readings at the associated pressure sensor (42). If a channel (210, 212, 213, 214, 217, 218) is blocked, the predetermined flow rate will trigger pressure sensor (42), indicating the inability to adequately pass this flow rate. As pumps (32) are peristaltic in the present example, their operating flow rate combined with the percentage of time they are cycled off due to pressure will provide the actual flow rate. The flow rate can also be estimated based upon the decay of the pressure from the time pump (32) cycles off.

At the end of the wash cycle, drain pump (72) is activated to remove detergent solution (86) from basin (14a) and channels (210, 212, 213, 214, 217, 218). Drain pump (72) turns off when drain level sensor (76) indicates that drainage is complete. During the drain process, sterile air is blown through all channels (210, 212, 213, 214, 217, 218) of endoscope (200) simultaneously to minimize potential carryover.

After the wash cycle is complete, reprocessing system (2) begins a rinse cycle. To initiate this rinse cycle, basin (14a) is again filled with warm water (e.g., at approximately 35° C.). Water temperature is controlled by controlling the mix of heated and unheated water. The water level is detected by pressure sensor (59). The rinse water is circulated within channels (210, 212, 213, 214, 217, 218) of endoscope (200) via channel pumps (32); and over the exterior of endoscope (200) via circulation pump (70) and sprinkler arm (60) for a certain period of time (e.g., one minute). As rinse water is pumped through channels (210, 212, 213, 214, 217, 218), the flow rate through channels (210, 212, 213, 214, 217, 218) is measured and if it falls below the predetermined rate for any given channel (210, 212, 213, 214, 217, 218), that channel (210, 212, 213, 214, 217, 218) is identified as blocked, the program is stopped, and the operator is notified of the condition.

At the end of the rinse cycle, drain pump (72) is activated to remove the rinse water from basin (14a) and channels (210, 212, 213, 214, 217, 218). Drain pump (72) turns off when drain level sensor (76) indicates that drainage is complete. During the drain process, sterile air is blown through all channels (210, 212, 213, 214, 217, 218) of endoscope (200) simultaneously to minimize potential carryover. In some versions, the above-described rinsing and draining cycles are repeated at least once again, to ensure maximum rinsing of detergent solution (86) from the surfaces of endoscope (200) and basin (14a).

After reprocessing system (2) has completed the desired number of rinsing and drying cycles, reprocessing system (2) proceeds to a disinfection cycle. To initiate the disinfection cycle, basin (14a) is filled with very warm water (e.g., at approximately 53° C.). Water temperature is controlled by controlling the mix of heated and unheated water. The water level is detected by pressure sensor (59). During the filling process, channel pumps (32) are off in order to ensure that the disinfectant solution in basin (14a) is at the in-use concentration prior to circulating through channels (210, 212, 213, 214, 217, 218) of endoscope (200).

Next, a measured volume of concentrated stock solution (92) is drawn from disinfectant metering pre-chamber (96) and delivered into the water, i.e., diluted, in basin (14a) via metering pump (100) to make a dose of diluted or "in-use" disinfectant solution. The volume of concentrated stock solution (92) is controlled by the positioning of fill level switch (98) relative to the bottom of metering pre-chamber (96). Metering pre-chamber (96) is filled until fill level switch (98) detects liquid. Concentrated stock solution (92) is drawn from metering pre-chamber (96) until the level of concentrated stock solution (92) in metering pre-chamber (96) is just below the tip of metering pre-chamber (96). After the necessary volume is dispensed, metering pre-chamber (96) is refilled from the bottle of concentrated stock solution (92). Concentrated stock solution (92) is not added until basin (14a) is filled, so that in case of a water supply problem, concentrated disinfectant is not left on endoscope (200) with no water to rinse it. While concentrated stock solution (92) is being added, channel pumps (32) are off in order to ensure that concentrated stock solution (92) in basin (14a) is diluted to desired in-use concentration prior to circulating through channels (210, 212, 213, 214, 217, 218) of endoscope (200).

In-use disinfectant solution is actively pumped throughout internal channels (210, 212, 213, 214, 217, 218) by pumps (32) and over the outer surface of endoscope (200) by circulation pump (70). This may be done for any suitable duration (e.g., at least 5 minutes). The temperature of in-use disinfectant solution may be controlled by in-line heater (80) to stay at a consistent temperature (e.g., about 52.5° C.). During the disinfection process, flow through each channel (210, 212, 213, 214, 217, 218) of endoscope (200) is verified by timing the delivery of a measured quantity of solution through channel (210, 212, 213, 214, 217, 218). Valve (S1) is closed, and valve (S7) opened, and in turn, each channel pump (32) delivers a predetermined volume to its associated channel (210, 212, 213, 214, 217, 218) from metering tube (136). This volume and the time it takes to deliver the volume, may provide a very accurate flow rate through the channel (210, 212, 213, 214, 217, 218). Anomalies in the flow rate from what is expected for a channel (210, 212, 213, 214, 217, 218) of that diameter and length are flagged by control system (20) and the process stopped. As in-use disinfectant solution is pumped through channels (210, 212, 213, 214, 217, 218), the flow rate through channels (210, 212, 213, 214, 217, 218) is also measured as described above.

At the end of the disinfection cycle, drain pump (72) is activated to remove spent disinfectant solution from basin (14a) and channels (210, 212, 213, 214, 217, 218). During the draining process, sterile air is blown through all channels (210, 212, 213, 214, 217, 218) of endoscope (200) simultaneously to minimize potential carryover. As will be described in greater detail below, used disinfectant solution is discarded. However, prior to being discarded, a sample of used disinfectant solution may be tested to determine whether the concentration of disinfectant agent in the used disinfectant solution is within an acceptable range, and this information is utilized in the preparation of a new dose of in-use disinfectant solution for use in a subsequent disinfection cycle.

In some versions, reprocessing system (2) comprises one or more integral concentration sensors to measure parameters relating to one or more reprocessing fluids such as, for example, concentrated stock solution, disinfectant (e.g., disinfectant that has been diluted to an "in-use" concentration or disinfectant that is supplied already at the "in-use" concentration), detergent, diluent (e.g., water), alcohol and/or any other suitable fluid that circulates through reprocessing system (2). As described above, basin drain (62) drains used disinfectant solution from basin (14a) into sump (64) for collection, and in some examples, recirculation pump (70) recirculates the disinfectant solution drained from basin drain (62) and sump (64) to spray nozzle assembly (60), which sprays recirculated disinfectant solution into the basin (14a) and onto medical device (200). Concentration sensors (not shown) may be positioned, for example, at various locations along the recirculation line, such as immediately downstream from sump (64) or downstream from recirculation pump (70), as shown, to detect, for example, the concentration of the decontaminant in the disinfectant solution drained from basin drain (62), i.e., the in-use reprocessing fluid concentration.

The concentration sensor(s) may be operatively connected to and controlled by control system (20). Concentration sensor(s) may provide input "I" to the microcontroller to communicate the concentration of disinfectant in the used disinfectant solution. The programmable memory of the microprocessor of the controller (20) may store concentration data along with other flow parameters, including volume, temperature, flow rate, cycle time, and the like. In various examples, the programmable memory of the microprocessor of controller (20) may store process and concentration data from one or more previous disinfection cycles of reprocessing system (2). Controller (20) may calculate an amount of disinfectant to add to diluent to provide in-use disinfectant solution having a target disinfection concentration for use in a subsequent disinfection cycle. As described above, the microcontroller may provide an output O to metering pumps (88 and/or 100) to meter a precise quantity of disinfectant to the recirculating used disinfectant solution as needed.

Figure 6:
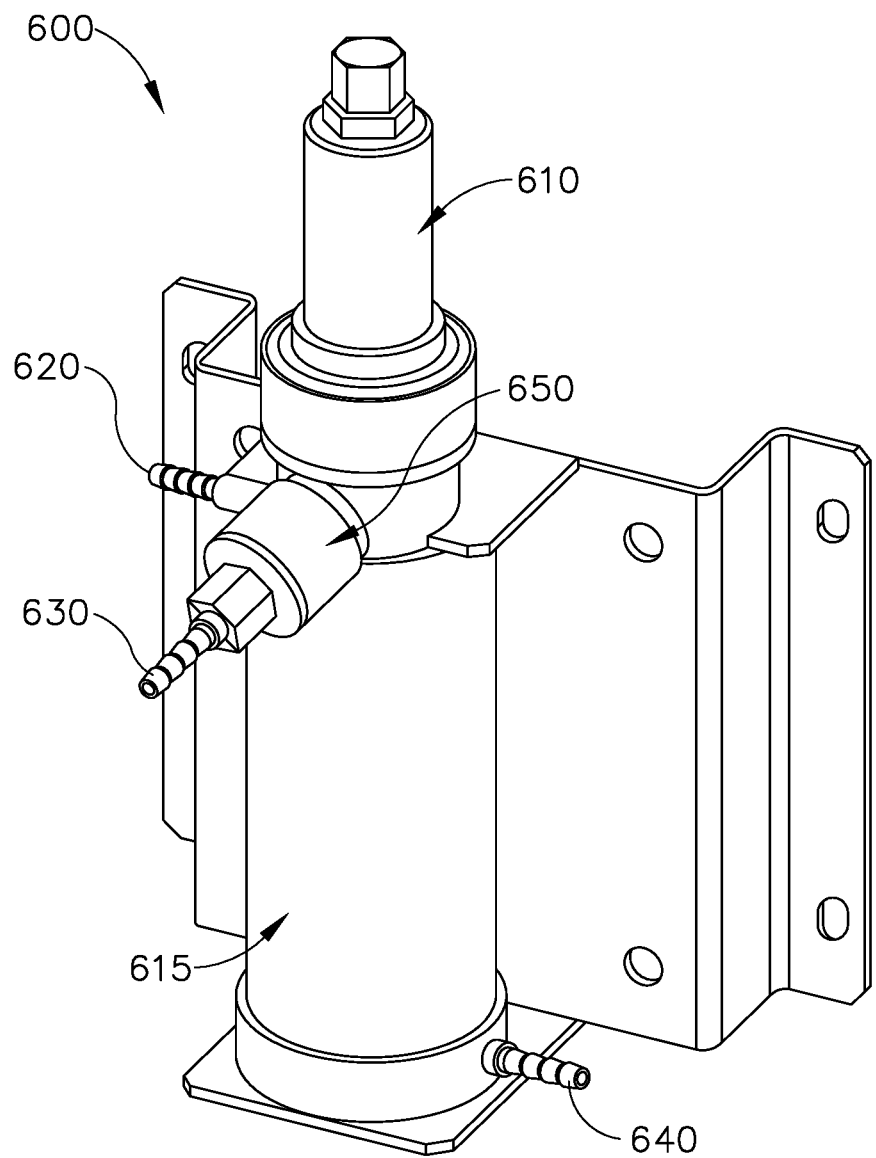
FIG. 6 depicts a perspective view of an exemplary concentration sensor for use in the reprocessing system of FIG. 1.
Figure 7:
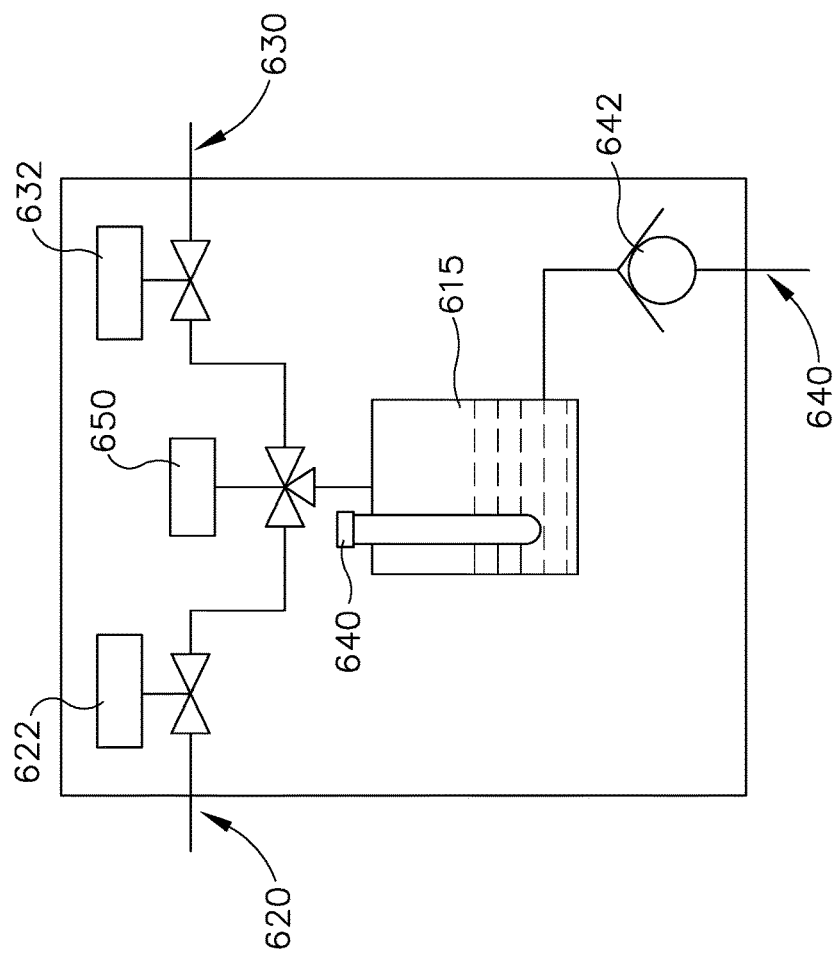
FIG. 7 depicts a schematic diagram showing components of the concentration sensor of FIG. 6.

FIGS. 6-7 show an exemplary form that a concentration sensor may take. In particular, FIGS. 6-7 show an exemplary concentration sensor (600) that comprises a measuring cell (610), a sensor chamber (615), a first inlet (620), a second inlet (630), an outlet (640), and a selector valve (650) (e.g., a three-way valve). First inlet (620) is in fluid communication with first basin (14a). Second inlet (630) is in fluid communication with second basin (14b). Selector valve (650) is operable to selectively place either first inlet (620) or second inlet (630) in fluid communication with sensor chamber (615). In versions where just a single basin (14a) is used, second inlet (630) and selector valve (650) may be omitted.

Measuring cell (610) may comprise an optical sensor, an electrochemical sensor, and/or any other suitable kind of sensor. An exemplary electrochemical sensor is commercially available from JUMO Process Control, Inc. (New York, N.Y.). An exemplary optical sensor is generally described in U.S. Pat. No. 7,879,289, which is incorporated by reference herein. Measuring cell (610) may detect the concentration of disinfectant in the used disinfectant solution. Concentration sensor (600) may further comprise a temperature sensor (not shown) to detect the temperature of the used disinfectant solution in sensor chamber (615) in order to dynamically adjust disinfectant concentration and/or time of exposure of medical instrument (200) to in-use disinfectant solution utilized in subsequent disinfection cycle(s), as is described in further detail below.

As shown in FIG. 7, a first valve (622) may be interposed between first inlet (620) and selector valve (650), though it should be understood that first valve (622) is merely optional. Similarly, a second valve (632) may be interposed between second inlet (630) and selector valve (650), though it should be understood that second valve (632) is merely optional. FIG. 7 also shows a check valve (642) interposed between sensor chamber (615) and outlet (640), thereby preventing backflow via outlet (640) into sensor chamber (615) while allowing fluid to flow from sensor chamber (615) to outlet (640). Again, check valve (642) is merely optional.

In an exemplary use, at least a portion of used disinfectant solution may flow from basin drain (62) and sump (64) to the corresponding inlet (620, 630), and ultimately into sensor chamber (615) for testing. Valves (622, 632, 650) may be actuated to provide a state where used disinfectant solution flows from the appropriate basin (14a, 14b) into sensor chamber (615). If the used disinfectant solution is coming from basin (14a), valve (622) may be in an open state while valve (632) is in a closed state. If the used disinfectant solution is coming from basin (14b), valve (632) may be in an open state while valve (622) is in a closed state. By way of example only, a sample of used disinfectant solution may be pulled for testing from the recirculation line at regular or intermittent intervals, as desired. A sample of used disinfectant solution may be pulled into sensor chamber (615) for testing during or following a disinfection cycle of the disinfection process. Circulating used disinfectant solution collected in sump (64) from a previous disinfection cycle may be tested by concentration sensor (600) while it is, for example, being recycled back to spray nozzle assembly (60) for a subsequent disinfection cycle.

When a sample of used disinfectant solution is pulled from the recirculation line to test its concentration, valves (622, 632, 650) may be actuated to allow a small portion of the circulating fluid to flow into sensor chamber (615). Measuring cell (610) may be in fluid communication with sensor chamber (615) and in some versions may be positioned in sensor chamber (615). Measuring cell (610) then measures the concentration of the disinfectant in the used disinfectant solution, for example, the in-use concentration of peracetic acid, in the sample, and relays that information to control system (20) as input "I," the data for which is stored and may be used to upwardly adjust concentration levels of concentrated stock solution in disinfectant solution in subsequent disinfection cycle(s). Following testing, the sample may flow from sensor chamber (615) via outlet (640) to various locations, including, for example, a utility drain, a sample collection chamber for additional testing, back to the recirculation line, and/or directly to spray nozzle assembly (60) for further disinfection.

A plurality of concentration values may be stored in a look-up table defined within programmable memory on a microprocessor of controller (20). The values of the expected disinfectant concentration in the used disinfectant solution in the look-up table may be theoretically predicted and/or the values may be empirically tested and then stored in the programmable memory. Once the disinfectant concentration in the used disinfectant solution has been communicated to controller (20), the microprocessor may derive a target or predetermined disinfectant concentration from the look-up table and compare the actual used disinfectant concentration to a target concentration. In some cases, the actual disinfectant concentration in the used disinfectant solution may not exactly match the target concentration and, thus, the microcontroller may command pumps (32 and/or 100) to meter a precise quantity of diluent (e.g., water) and/or disinfectant, respectively, to obtain an in-use disinfectant concentration between a minimum target value and a maximum target value in the disinfection solution in subsequent disinfection cycle(s).

Adjustment in the concentration level of the disinfectant in the in-use disinfectant solution may be made upstream based on a single test for the previous disinfection cycle or may be based on a rolling average of several previous disinfection cycles. For example, the concentration level of disinfectant in the in-use disinfection solution may be made based on the rolling average of the previous 5 disinfection cycles. In a further example, it is contemplated that other parameters may be adjusted. For example, the temperature of the in-use disinfectant solution could be adjusted to be more or less effective (i.e., more or less active against microbes). For example, based on disinfectant concentration values in the in-use disinfectant solution, the temperature of the in-use disinfectant solution could be increased to be more effective against microbes or, conversely, the temperatures of the in-use solution could be actively cooled (or not heated) if the concentration values were too high.

Based upon temperature and/or concentration values of disinfectant in the used disinfectant solution, controller (20) may be utilized to adjust concentration level of the disinfectant in the in-use disinfectant solution and/or its temperature and/or exposure time in subsequent disinfection cycle(s). Additional or alternative properties may also be adjusted by controller (20) based upon temperature and/or concentration values of disinfectant in the used disinfectant solution. For example, controller (20) may adjust at least one property of at least one subsequent disinfection cycle, wherein the at least one property is selected from disinfectant concentration, disinfectant volume, disinfectant temperature, disinfectant flow rate, diluent concentration, diluent volume, diluent temperature, diluent flow rate, disinfection cycle time and combinations thereof by controller (20) as necessary to maintain the minimum effective concentration of the disinfectant in in-use disinfectant solution during at least one subsequent disinfection cycle.

In addition to or in lieu of the foregoing, a number of alternative techniques may be utilized for measuring disinfectant agent concentration in the disinfectant solution between the disinfection cycles of a reprocessing system (2). For example, an operator of reprocessing system (2) may expose a test strip to a sample of used disinfectant solution from a given disinfection cycle and observe the strip for color change that is indicative of a disinfectant agent concentration that is below a minimum effective concentration. Alternatively, an automated system for measuring disinfectant agent concentration in the disinfectant solution may be utilized. An example of a useful automated system is described in U.S. patent application Ser. No. 15/157,952, entitled "Apparatus and Method to Measure Concentration of Disinfectant in Medical Device Reprocessing System," filed on May 18, 2016 and incorporated by reference herein.

In any case, once a concentration of disinfectant agent in the used disinfectant solution is measured, dilution of concentrated stock solution (92) may be adjusted to provide for an effective and minimally harmful dose of disinfectant solution for use in a subsequent disinfection cycle of reprocessing system (2). Additional factors such as shelf-life of disinfectant agent may be utilized to calculate actual concentration of disinfectant agent in concentrated stock solution (92). Taking factors such as these into account, a method of dynamically preparing an effective, yet minimally harmful dose of disinfectant solution from concentrated stock solution (92) is described in detail below. Alternatively, if the disinfectant cannot be adjusted, the exposure time and/or temperature may be adjusted to provide an effective and minimally harmful exposure to the disinfectant.

After used disinfectant solution has been drained from basin (14a), reprocessing system (2) begins a final rinse cycle. To initiate this cycle, basin (14a) is filled with sterile warm water (e.g., at approximately 45° C.) that has been passed through a filter (e.g., a 0.2 µm filter). The rinse water is circulated within channels (210, 212, 213, 214, 217, 218) by pumps (32); and over the exterior of endoscope (200) via circulation pump (70) and sprinkler arm (60) for a suitable duration (e.g., 1 minute). As rinse water is pumped through channels (210, 212, 213, 214, 217, 218), the flow rate through channels (210, 212, 213, 214, 217, 218) is measured as described above. Drain pump (72) is activated to remove the rinse water from basin (14a) and channels (210, 212, 213, 214, 217, 218). During the draining process, sterile air is blown through all channels (210, 212, 213, 214, 217, 218) of endoscope (200) simultaneously to minimize potential carryover. In some versions, the above-described rinsing and draining cycles are repeated at least two more times, to ensure maximum rinsing of disinfectant solution residuals from the surfaces of endoscope (200) and basin (14a).

After the final rinse cycle is complete, reprocessing system (2) begins a final leak test. In particular, reprocessing system (2) pressurizes the body of endoscope (200) and measures the leak rate as described above. If the final leak test is successful, reprocessing system (2) indicates the successful completion of the cycles via touch-screen (22). From the time of program completion to the time at which lid (16a) is opened, pressure within the body of endoscope (200) is normalized to atmospheric pressure by opening vent valve (S5) at a predetermined rate (e.g., valve (S5) opened for 10 seconds every minute).

Depending on customer-selected configuration, reprocessing system (2) may prevent lid (16a) from being opened until a valid user identification code is entered. Information about the completed program, including the user ID, endoscope ID, specialist ID, and patient ID are stored along with the sensor data obtained throughout the program. If a printer is connected to reprocessing system (2), and if requested by the operator, a record of the disinfection program will be printed. Once a valid user identification code has been entered, lid (16a) may be opened (e.g., using the foot pedal as described above). Endoscope (200) is then disconnected from flush lines (30) and removed from basin (14a). Lid (16a) can then be closed using both the hardware and software buttons as described above.

III. Exemplary Method for Dynamic Dosing of Disinfectant Solution

As noted above, reprocessing system (2) provides metered dosage of concentrated stock solution (92), which is diluted with water before reaching endoscope (200). In some instances, concentrated stock solution (92) may be dosed out for usage in reprocessing system (2) over a protracted period of time. Consequently, disinfectant agent in the concentrated stock solution (92) may become unstable and/or degrade, thereby reducing the potency of the concentrated stock solution (92). For example, an effective concentration of peracetic acid may be reduced by as much as half in as little as 72 hours when stored at 45° C. In the event that the potency of concentrated stock solution (92) has degraded, the in-use disinfection solution that is created using the concentrated stock solution (92) may have an unacceptably low concentration of disinfectant if the diluent (e.g., water) is combined with an amount of disinfectant that is assumed to have non-degraded potency. In other words, the in-use disinfection solution may not perform as well as expected when degraded concentrated stock solution (92) is used.

In order to compensate for any reduced activity of disinfectant agent in a concentrated stock solution (92), reprocessing system (2) may be configured to assume that the "worst case scenario" has taken place, i.e., that the disinfectant agent in concentrated stock solution (92) has undergone maximum degradation. To compensate for the worst case scenario, dilution of concentrated stock solution (92) may be decreased, such that a greater volume of concentrated stock solution (92) is diluted with water (or other diluent), when preparing in-use disinfectant solution for use in subsequent disinfection cycle(s).

As another scenario, there may be instances where the diluent (e.g., water) in concentrated stock solution (92) has evaporated excessively, which will result in a concentration of disinfectant agent in concentrated stock solution (92) that is higher than expected. In such scenarios, it may be desirable to either reduce the volume of concentrated stock solution (92) that is combined with water (or other diluent) when preparing in-use disinfectant solution or increase the volume of water (or other diluent) that is combined with a consistent volume of concentrated stock solution (92) when preparing in-use disinfectant solution.

By relying on assumptions of disinfectant agent concentration in concentrated stock solution (92), a number of problems may result. For example, an endoscope (200) that is reprocessed in reprocessing system (2) may be exposed to unnecessarily high concentrations of disinfectant agent, which may in turn shorten the useful life of endoscope (200) and/or parts thereof. Moreover, under-dilution of concentrated stock solution (92) may result in costly and unnecessary waste of concentrated stock solution (92).

Utilizing a fixed time for exposure of a medical device to disinfectant solution regardless of the concentration of disinfectant agent and/or the temperature at which disinfection occurs, may also result in inefficiencies. For example, if a disinfectant solution is assumed to have a disinfectant agent concentration lower than the target concentration, the temperature of the disinfectant solution being dispensed into basin (14a, 14b) may be set artificially higher than the temperature that would otherwise be required. Likewise, the exposure time of medical instrument (200) to disinfectant solution may be unnecessarily longer than needed to be efficacious. As a result, the medical instrument (200) reprocessing cycle may be longer than needed simply to accommodate the "worst case scenario." It follows that longer reprocessing cycles may in turn lead to reduced reprocessing output.

The below described apparatus and method of dynamic dosing of concentrated stock solution (92) may overcome these and a number of related problems. In general, the method comprises providing an initial dose of in-use disinfectant solution comprising a desired target concentration of disinfectant agent, measuring the concentration of disinfectant agent in the used disinfectant solution after use, and increasing, as needed, the amount of concentrated stock solution (92) that is diluted to make in-use disinfectant solution for use in subsequent disinfection cycle(s). In some exemplary methods, exposure time of a medical device to in-use disinfectant solution may optionally be adjusted based upon the temperature of the in-use disinfectant solution and the measurement of the concentration of disinfection agent in the used disinfectant solution. In any case, in the examples described below, the methods are automated, thereby eliminating the need for manual monitoring and/or manual dilution of solutions.

Figure 4:
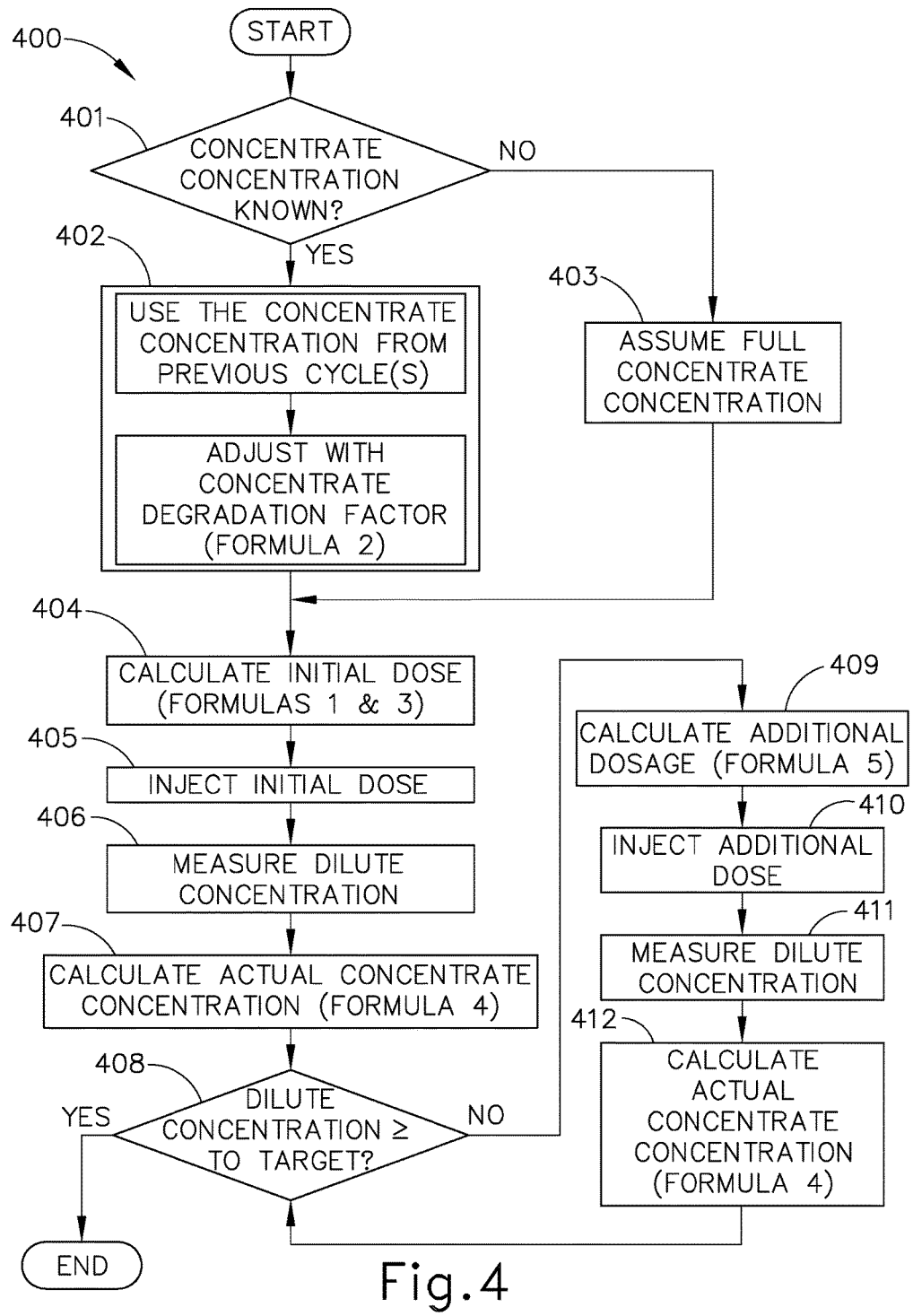
FIG. 4 depicts a block diagram of a method for dynamic dosing of disinfectant solution in a reprocessing system as shown in FIG. 1.

FIG. 4 is a block diagram depicting an exemplary method (400) of dynamic dosing of concentrated stock solution (92). As shown in FIG. 4, dynamic dosing of concentrated stock solution (92) begins with a query (block 401) of whether the concentration of disinfectant agent in concentrated stock solution (92) is known.

If the answer to the query (block 401) is "no," then it is assumed (block 403) that disinfectant agent is at its original concentration in the concentrated stock solution (92), i.e., no degradation of the disinfectant agent has occurred. An initial dose, i.e., volume, of concentrated stock solution (92) to be diluted to make in-use disinfectant solution containing a desired concentration of disinfectant agent is calculated (block 404). An exemplary formula for use in calculating the initial dose of concentrated stock solution (92), is as follows:

$$V = \frac{DW}{C - D} \qquad \text{Formula 1}$$

Wherein:
V=initial dose, i.e., volume of concentrated stock solution (92) to be dispensed and diluted;
D=concentration of disinfectant agent in in-use disinfectant solution (prior to being used in disinfection cycle);
W=water (or other diluting fluid) volume; and
C=concentration of disinfectant agent in concentrated stock solution (92).

For example, if the concentration of the disinfectant agent peracetic acid in concentrated stock solution (92) is 15 vol % and 4,000 mL of in-use disinfectant solution containing a target concentration of 0.15 vol % peracetic acid is desired, then the initial dose, i.e., volume of concentrated stock solution (92) to be dispensed into water (or other diluting fluid) is calculated as follows:

$$V = \frac{0.15\% \ (4000 \ \text{ml})}{15\% - 0.15\%} = 40.4 \ \text{mL}$$

Thus, in this example, 40.4 mL of concentrated stock solution (92) would be dispensed into water (or other diluting fluid) that is present in basin (14a, 14b) of reprocessing system (2).

If, on the other hand, the answer to the query (block 401) is "yes," then the known (i.e., measured) concentration or the known average disinfectant agent concentration from previous disinfection cycle(s), is adjusted (block 402) to account for degradation of disinfectant agent.

Accounting for degradation of disinfectant agent in concentrated stock solution (92) (block 402) may be accomplished by calculating degradation rate of disinfectant agent in concentrated stock solution (92) and utilizing the results of the calculation to adjust, if needed, the volume of concentrated stock solution (92) to be dosed in the preparation of in-use disinfectant solution for a subsequent disinfection cycle.

While the concentration of the disinfectant agent peracetic acid in concentrated stock solution (92) is expressed as vol % in the present example, it should be understood that any suitable units (e.g., ppm) may be used. In addition, while peracetic acid is used as the disinfectant agent in the present example, it should be understood that various other kinds of disinfectant agents may be used, including but not limited to glutaraldehyde, hydrogen peroxide, ozone, or ortho-phthalaldehyde. By way of further example only, in some versions where ortho-phthalaldehyde is used as the disinfectant agent, the ortho-phthalaldehyde may be provided at an initial concentration of about 5.75 vol % in concentrated stock solution (92); and then be diluted to a target concentration of about 0.07 vol % in in-use disinfectant solution. As another merely illustrative example, ortho-phthalaldehyde may be diluted to a target concentration of about 0.3 vol % in in-use disinfectant solution.

An exemplary method of calculating degradation rate of a disinfectant agent utilizes a comparison of the concentration of disinfectant agent in concentrated stock solution (92) from two previous disinfection cycles that are performed within a known time interval, using the following formula:

$$A = \frac{C2 - C1}{t2 - t1} = \frac{\Delta C}{\Delta T} \qquad \text{Formula 2}$$

Wherein:
$A$=degradation rate of disinfectant agent in concentrated stock solution (92);
$C_1$=concentration of disinfectant agent in concentrated stock solution (92) from a first cycle;
$C_2$=concentration of disinfectant agent in concentrated stock solution (92) from a second cycle;
$T_1$=start time the first cycle; and
$T_2$=start time of the second cycle.

In addition to being useful for the calculation of degradation rate of disinfectant agent in concentration stock solution (92) between cycles, Formula 2 may be alternatively used to calculate the degradation rate during prolonged periods in which the concentrated stock solution (92) is not in use, such as over the course of a holiday and/or weekend, and/or during shipment of the concentrated stock solution (92) from the manufacturer. In such circumstances, rather than representing the difference in time between cycles (i.e., $T_2-T_1$), $\Delta T$ of Formula 2 is instead representative of the elapsed time during which the concentrated stock solution (92) is not in use.

Continuing with the previous example, if the concentration of disinfectant agent in concentrated stock solution (92) from the first cycle is 15 vol %, concentration of disinfectant agent in concentrated stock solution (92) from the second cycle is 14 vol %, start time of the first cycle is 1:00 PM and start time of the second cycle is 3:00 PM, then degradation rate may be calculated as follows:

$$A = \frac{14\% - 15\%}{3\ hr - 1\ hr} = -\frac{1\%}{2\ hr} = -0.5\% \text{ per } hr$$

Thus, a degradation rate of −0.5% per hour may be used in the calculation (block 404) of an initial dose, i.e., volume, of concentrated stock solution (92) to be diluted to make in-use disinfectant solution (92). To do so, the concentration, $C_3$, of disinfectant agent in concentrated stock solution (92) at the later time, $T_3$, when the in-use disinfectant solution is to be made, is first calculated utilizing the following exemplary formula:

$$C_3=C_2+A(T_3-T_2)=C_2+A\Delta T \qquad \text{Formula 3}$$

Wherein:
$C_3$=concentration of disinfectant agent in concentrated stock solution (92) at $T_3$;
$C_2$=concentration of disinfectant agent in concentrated stock solution (92) at $T_2$;
$A$=degradation rate;
$T_3$=start time of a third cycle; and
$T_2$=start time of the second cycle.

Continuing with the previous example, if the third cycle starts at 7:00 PM, the concentration, $C_3$, of disinfectant agent in concentration stock solution (92) at 7:00 PM is calculated as follows:

$$C_3=14\%+(-0.5\% \text{ per hr }(4\ hr))=12\%$$

Thus, the concentration of disinfectant agent in concentrated stock solution (92) at 7:00 PM is 12 vol %, a value which may then be utilized as the concentration of disinfectant agent in concentrated stock solution (92), "C," in Formula 1 above, in order to calculate the initial dose, i.e., volume of concentrated stock solution (92) to be dispensed into water (or other diluting fluid) at 7:00 PM pursuant to the initial dose calculation (block 404).

Once an initial dose of concentrated stock solution (92) is calculated (block 404), then the initial dose is automatically injected (block 405) into water (or other diluting fluid) that is present in basin (14a, 14b) where it is diluted to make a dose of in-use disinfectant solution (92) comprising the target concentration of disinfectant agent.

After the in-use disinfectant solution (92) is used to disinfect endoscope (200), the concentration of the disinfectant agent in the now "used" disinfectant solution is measured (block 406) using suitable means. Various suitable devices and techniques that may be used to measure the concentration of the disinfectant agent in the used disinfectant solution will be apparent to those of ordinary skill in the art in view of the teachings herein. By way of example only, the concentration of the disinfectant agent in the used disinfectant solution may be measured using electrochemistry, using optical techniques, and/or using any other suitable devices or techniques. Other suitable examples will be apparent to those of ordinary skill in the art in view of the teachings herein.

In the exemplary method (400), the concentration of the disinfectant agent in the used disinfectant solution is measured (block 406) via an automated system and utilized to calculate (block 407), the current or "actual" concentration of the concentrated stock solution (92). Based upon this information, it is determined whether an adjusted dose, i.e., an increased volume, of concentrated stock solution (92) should be diluted to make the in-use disinfectant solution for use in a subsequent disinfection cycle.

An exemplary formula for use in calculating the actual concentration of the concentrated stock solution (92) is as follows:

$$C' = \frac{D'(W+V')}{V'} \quad \text{Formula 4}$$

Wherein:
C'=actual concentration of concentrated stock solution (92);
D'=measured concentration of disinfectant agent in the used disinfectant solution;
W=water (or other diluting fluid) volume; and
V'=initial dose, i.e., volume of concentrated stock solution (92) diluted to make the in-use disinfectant solution.

Continuing with the previous example, assuming that the measured concentration of disinfectant agent in the used disinfectant solution, D', is 0.14 vol %, then the actual concentration, C', of the concentrated stock solution (92) is calculated as follows:

C'=0.14% (4000 mL+40.4 mL)/40.4 mL=14%

A query (block 408) of whether the actual concentration of the disinfectant agent in the concentrated stock solution (92), C', is greater than or equal to the assumed concentration of the disinfectant agent is undertaken.

If the answer to the query (block 408) is "yes," then the initial dose, i.e., volume of concentrated stock solution (92) to be dispensed into water (or other diluting fluid) to make the in-use disinfectant solution to be used in a subsequent disinfection cycle remains unchanged and the exemplary method of dynamic dosing ends (block 413).

If, on the other hand, the answer to the query (block 408) is "no," and the actual concentration of the disinfectant agent in the concentrated stock solution (92), C', is less than the assumed concentration of the disinfectant agent, then an additional dosage of concentrated stock solution (92) to be diluted is calculated (block 409). An exemplary formula for use in calculating the additional dosage, V2, of concentrated stock solution (92) that is needed to obtain the target concentration, Dt, of disinfectant reagent in the in-use disinfectant solution is as follows:

$$V2 = \frac{DtW}{C' - Dt} - V1 \quad \text{Formula 5}$$

Wherein:
V2=volume of additional dosage of concentrated stock solution (92);
Dt=target concentration of disinfectant reagent in the in-use disinfectant solution;
W=water (or other diluting fluid) volume;
C'=actual concentration of the concentrated stock solution (92); and
V1=volume of initial dosage of concentrated stock solution (92).

Continuing with the previous example, an additional dosage, V2, of concentrated stock solution (92) to be diluted to obtain the target concentration of 0.15 vol % of disinfectant agent in the in-use disinfectant solution is calculated as follows:

$$V2 = \frac{0.15\% \, (4000 \text{ ml})}{14\% - 0.15\%} - 40.4 = 2.91 \text{ mL}$$

Thus, an additional dosage, in the present example 2.91 mL, of concentrated stock solution (92) is injected (block 410) into basin (14a, 14b) where it is diluted, along with the initial dose of concentrated stock solution (92), with water (or other diluting fluid) to make a dose of in-use disinfectant solution comprising the target concentration of disinfectant agent.

After the in-use disinfectant solution is used to disinfect endoscope (200), the concentration of the disinfectant agent in the now "used" disinfectant solution is measured (block 411) using any suitable devices and techniques as noted above with reference to the earlier concentration measurement (block 406).

The concentration of the disinfectant agent in the used disinfectant solution is used to calculate (block 412) the current or "actual" concentration of concentrated stock solution (92), for example using Formula 4 (above). Once the calculation of the current or "actual" concentration of the concentrated stock solution (92) occurs (block 412), the query (block 408), described above, is repeated to determine whether the actual concentration of the disinfectant agent in concentrated stock solution (92) is greater than or equal to the assumed concentration of the disinfectant agent.

If the answer to the repeated query (block 408) is "yes", then the initial dose, i.e., volume of concentrated stock solution to be dispensed into water (or other diluting fluid) to make the in-use disinfectant solution to be used in a subsequent disinfection cycle remains unchanged and the exemplary method of dynamic dosing ends (block 413).

If, on the other hand, the answer to the repeated query (block 408) is "no," and the actual concentration of the disinfectant agent in the concentrated stock solution is less than the assumed concentration of the disinfectant agent, then steps set forth in blocks 409 through 412 are repeated as needed.

The exemplary method for dynamic dosing of disinfectant solution may be repeated as needed and/or restarted (block 401) after a fresh concentrated stock solution (92) is newly added into the reprocessing system (2).

Some exemplary methods for dynamic dosing of concentrated stock solution (92) may comprise adjusting the exposure time of a medical device (200) to in-use disinfectant solution based upon measured dilute concentration of in-use solution (block 406) in a previous disinfection cycle or cycles. Adjustment of the exposure time may be based upon a pre-determined relationship between minimum exposure time, over a range of in-use disinfectant solution temperatures and over a range of disinfectant agent concentrations in a concentrated stock solution (92). The latter range might include a highest concentration of disinfectant agent in concentrated stock solution (92) in accordance with manufacturer specifications, to a lowest concentration of disinfectant agent in concentrated stock solution (92) at the end of the disinfectant agent's shelf-life.

In any case, the lowest temperature of the in-use disinfectant solution when it is present in basin (14a, 14b) is measured. Using the pre-determined relationship described above, exposure time of a medical instrument (200) during the subsequent disinfection cycle may then be adjusted, i.e., shortened or lengthened, by responding to actual concentration of disinfectant agent in, and temperature of, the in-use disinfectant solution from a previous cycle or average of previous cycles. Thus, this optional step may eliminate inefficiencies resulting from relying upon "worst case scenario" estimations of temperature and concentration of solutions. By way of example only, when the concentration of disinfectant agent in the in-use disinfectant solution is at about 0.3 vol %, and the temperature is about 20° C., medical instrument (200) may be exposed to the in-use disinfectant solution for about 12 minutes. When the concentration of disinfectant agent in the in-use disinfectant solution is at about 0.3 vol %, and the temperature is about 25° C., medical instrument (200) may be exposed to the in-use disinfectant solution for about 5 minutes. When the concentration of disinfectant agent in the in-use disinfectant solution is at about 0.055 vol %, and the temperature is about 50° C., medical instrument (200) may be exposed to the in-use disinfectant solution for about 5 minutes.

Figure 5:
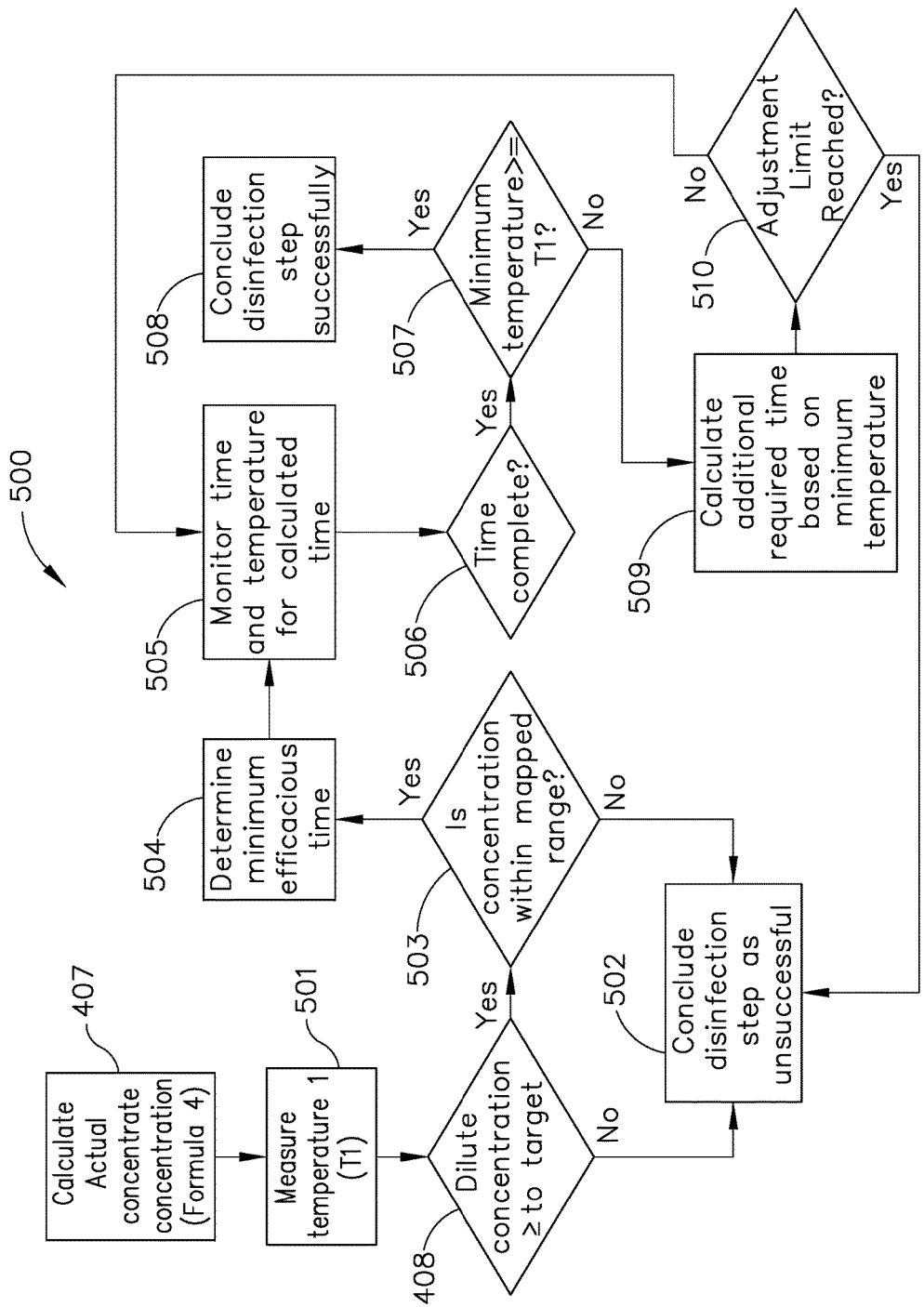
FIG. 5 depicts a block diagram of an exemplary method of dynamically adjusting exposure time of a medical device to disinfectant solution using the reprocessing system of FIG. 1.

FIG. 5 shows an exemplary method of dynamically adjusting the exposure time of a medical device (200) to in-use disinfectant solution in a subsequent disinfection cycle based upon a calculation of actual concentrate concentration of used solution (block 407) from a previous disinfection cycle or cycles pursuant to FIG. 4, and measurement of the actual temperature of the used solution in a previous disinfection cycle pursuant to FIG. 5.

As shown in FIG. 4, a query (block 408) is provided to determine whether the actual concentration of the disinfectant agent in the concentrated stock solution (92), C', is greater than or equal to the target concentration of the disinfectant agent in previous cycle(s). As shown in FIG. 5, either simultaneously or concurrently, actual temperature (T1) of in-use disinfectant solution from the previous disinfection cycle is measured (block 501).

If the answer to the query (block 408) is "no," then it is concluded that disinfection of medical instrument (200) was unsuccessful (block 502).

If the answer to the query (block 408) is "yes," a further query (block 503) whether actual temperature (T1) of used disinfectant solution that has been measured (block 501) is within an efficacious range (or alternatively, above an efficacious minimum temperature) so as to sufficiently disinfect medical instrument (200) is undertaken.

If the answer to the query (block 503) is "no," then it is concluded that disinfection of medical instrument (200) was unsuccessful (block 502).

If the answer to the query (block 503) is "yes," then a range of time for efficacious exposure of medical instrument (200) to in-use disinfectant solution in a subsequent disinfection cycle is calculated (block 504).

Actual time of exposure of medical instrument (200) to in-use disinfectant solution and actual temperature of in-use disinfectant solution in the subsequent disinfection cycle, now referred to as the "current" disinfection cycle, is monitored (block 505).

A query (block 506) is then undertaken to determine whether the completed time of exposure of medical instrument (200) to in-use disinfectant solution in the current disinfection cycle is within the range of time for efficacious exposure of medical instrument (200) to in-use disinfection solution.

Once the answer to the query (block 506) is "yes," then a query (block 507) is undertaken to determine whether temperature (T1) of in-use disinfection solution is within an efficacious range (or alternatively, above an efficacious minimum temperature). If the answer to the query (block 507) is "yes," then it is concluded (block 508) that the current disinfection cycle was successful and no additional time is added to the current disinfection cycle. If the answer to the query (block 507) is "no," then a calculation (block 509) of additional time required for successful disinfection of medical instrument (200) is undertaken.

A query (block 510) is then undertaken to determine whether the calculated additional time required is above a time limit that may be reasonably implemented in the current disinfection cycle. If the answer to the query (block 510) is "yes," then it is concluded that disinfection of medical instrument (200) was unsuccessful (block 502). If the answer to the query (block 510) is "no," then medical device (200) is exposed to in-use disinfection solution for the additional calculated time, while actual time of exposure of medical instrument (200) to in-use disinfectant solution and actual temperature of in-use disinfectant solution in the current disinfection cycle is once again monitored (block 505).

A query (block 506) is then provided to determine whether the completed additional time of exposure of medical instrument (200) to in-use disinfectant solution in the current disinfection cycle is within the range of time for efficacious exposure of medical instrument (200) to in-use disinfection solution.

Once the answer to the query (block 506) is "yes," then a query (block 507) is undertaken as to whether temperature (T1) is within the predetermined range (or alternatively, above a predetermined minimum temperature). If the answer to the query (block 507) is "yes," then it is concluded (block 508) that current disinfection cycle was successful and no additional time is added to the disinfection cycle. If the answer to the query (block 507) is "no," then a calculation (block 509) of additional time required for successful disinfection of medical instrument (200) is undertaken. A query (block 510) is then undertaken to determine whether the additional time required is above a time limit that may be reasonably implemented in the current disinfection cycle. If the answer to the query (block 510) is "yes," then it is concluded that disinfection of medical instrument (200) was unsuccessful (block 502). If the answer to the query (block 510) is "no," then the steps set forth in blocks 505 through 509 are repeated until such time as it is concluded that current disinfection cycle was successful (block 508) or until the calculated additional time (block 509) is determined (block 510) to be above a time limit that may be reasonably implemented in the disinfection cycle.

The exemplary method (500) as shown in FIG. 5, may be performed by an apparatus comprising a microcontroller (e.g., microcontroller (28) referred to above) and/or any other kind of control module that is operable to perform any necessary calculations in relation to the steps set forth in FIG. 5 above, in order to control additional exposure time of medical instrument (200) to in-use disinfection solution. Various suitable kinds of hardware components and arrangements thereof that may be used to perform method will be apparent to those of ordinary skill in the art in view of the teachings herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method for dynamic dosing of disinfectant solution in a medical device reprocessing system, comprising: (a) calculating a volume of an initial dose of concentrated disinfectant solution for dilution to make a first in-use disinfectant solution comprising a target concentration of disinfectant agent; (b) diluting the initial dose of concentrated disinfectant solution with diluting fluid to make the first in-use disinfectant solution comprising the target concentration of disinfectant agent; (c) applying the first in-use disinfectant solution to a first medical device; (d) measuring a concentration of the disinfectant agent in the first in-use disinfectant solution after applying it to the first medical device; (e) calculating actual concentration of the disinfectant agent in the concentrated disinfectant solution based upon the concentration of disinfectant agent in the first in-use disinfectant solution after applying it to the medical device; and (f) determining whether: (i) a volume of a second dose of concentrated disinfectant solution is increased compared to the volume of the initial dose to make a second in-use disinfectant solution comprising the target concentration of disinfectant agent, or (ii) a volume of a second dose of concentrated disinfectant solution is about the same as the volume of the initial dose to make a second in-use disinfectant solution comprising the target concentration of disinfectant agent.

Example 2

The method of Example 1, further comprising assuming that the disinfectant agent in the concentrated disinfectant solution is un-degraded when calculating the volume of an initial dose of concentrated disinfectant solution for dilution to make a first in-use disinfectant solution comprising a target concentration of disinfectant agent.

Example 3

The method of any one or more of Examples 1 through 2, further comprising: (a) determining that the volume of the second dose of concentrated disinfectant solution is increased compared to the volume of the initial dose; (b) increasing the volume of the second dose compared to the volume of the initial dose; and (c) diluting the second dose with diluting fluid to make a second in-use disinfectant solution comprising the target concentration of disinfectant agent.

Example 4

The method of Example 3, further comprising: (a) adding the diluting fluid into a basin configured to receive the medical device; and (b) dispensing the second dose into the diluting fluid in the basin.

Example 5

The method of Example 4, further comprising dispensing the second dose into a pre-metering chamber.

Example 6

The method of any one or more of Examples 1 through 5, further comprising: (a) determining that the volume of the second dose of concentrated disinfectant solution is about the same as the volume of the initial dose to make a second in-use disinfectant solution comprising the target concentration of disinfectant agent; and (b) diluting the volume of the second dose of concentrated disinfectant solution with diluting fluid to make a second in-use disinfectant solution comprising the target concentration of disinfectant agent.

Example 7

The method of Example 6, comprising: (a) adding the diluting fluid into a basin configured to receive the medical device; and (b) dispensing the second dose into the diluting fluid in the basin.

Example 8

The method of Example 7, further comprising dispensing the second dose into a pre-metering chamber.

Example 9

The method of any one or more of Examples 1 through 8, further comprising applying the second in-use disinfectant solution to a second endoscope.

Example 10

The method of any one or more of Examples 1 through 9, further comprising: (a) applying the second in-use disinfectant solution to a second medical device; (b) measuring concentration of the disinfectant agent in the second in-use disinfectant solution after applying it to the second medical device; (c) calculating actual concentration of the disinfectant agent in the concentrated disinfectant solution based upon the concentration of disinfectant agent in the second in-use disinfectant solution after applying it to the second medical device; and (d) determining whether: (i) a volume of a third dose of concentrated disinfectant solution is increased compared to the volume of the second dose to make a third in-use disinfectant solution comprising the target concentration of disinfectant agent, or (ii) a volume of a third dose of concentrated disinfectant solution is about the same as the volume of the second dose to make a third in-use disinfectant solution comprising the target concentration of disinfectant agent.

Example 11

The method of any one or more of Examples 1 through 10, further comprising calculating a degradation rate of the disinfectant agent and diluting an additional volume of the concentrated disinfectant solution with diluting fluid to make the first in-use disinfectant solution comprising the target concentration of disinfectant agent.

Example 12

The method of any one or more of Examples 1 through 11, further comprising applying the first in-use disinfectant solution to a first endoscope.

Example 13

The method of any one or more of Examples 1 through 12, further comprising diluting an initial dose of concentrated disinfectant solution with dilution fluid to make an in-use disinfectant solution comprising a target concentration of disinfectant agents selected from: glutaraldehyde, hydrogen peroxide, ortho-phthalaldehyde, ozone, peracetic acid and combinations thereof.

Example 14

The method of Example 13, further comprising diluting the initial dose of concentrated disinfectant solution with water to make an in-use disinfectant solution comprising a target concentration of ortho-phthalaldehyde of about 0.07 vol %.

Example 15

The method of Example 13, further comprising diluting the initial dose of concentrated disinfectant solution with water to make an in-use disinfectant solution comprising a target concentration of peracetic acid of about 0.15 vol %.

Example 16

A method for dynamic dosing of disinfectant solution in an endoscope reprocessing system, comprising automated steps of: (a) calculating a volume of an initial dose of concentrated disinfectant solution for dilution to make a first in-use disinfectant solution comprising a target concentration of disinfectant agent; (b) dispensing water into a basin configured to receive a first endoscope; (c) dispensing the initial dose of concentrated disinfectant solution into the water to make the first in-use disinfectant solution comprising the target concentration of disinfectant agent; (d) circulating the first in-use disinfectant solution from the basin through a first endoscope; (e) collecting a sample of the first in-use disinfectant solution after circulating it through the first endoscope; (f) measuring a concentration of the disinfectant agent in the sample of the first in-use disinfectant solution; (g) calculating actual concentration of the disinfectant agent in the concentrated disinfectant solution based upon the concentration of disinfectant agent in the sample of first in-use disinfectant solution; and (h) determining whether: (i) a volume of a second dose of concentrated disinfectant solution is increased compared to the volume of the initial dose to make a second in-use disinfectant solution comprising the target concentration of disinfectant agent, or (ii) a volume of a second dose of concentrated disinfectant solution is about the same as the volume of the initial dose to make a second in-use disinfectant solution comprising the target concentration of disinfectant agent.

Example 17

The method of Example 16, further comprising: (a) calculating a degradation rate of the disinfectant agent in the concentrated disinfectant solution; (b) dispensing an additional volume of the concentrated disinfectant solution into the basin to account for degradation of the disinfectant agent; and (c) diluting the initial dose and the additional volume of the concentrated disinfectant solution with the water in the basin to make the first in-use disinfectant solution comprising the target concentration of disinfectant agent.

Example 18

The method of any one or more of Examples 16 through 17, further comprising: (a) determining that the volume of the second dose of concentrated disinfectant solution is increased compared to the volume of the initial dose; and (b) dispensing an increased volume of the second dose as compared to the volume of the initial dose of the concentrated disinfectant solution into the water in the basin to make a second in-use disinfectant solution.

Example 19

The method of Example 18, further comprising: (a) circulating the second in-use disinfectant solution from the basin through a second endoscope; (b) collecting a sample of the second in-use disinfectant solution after circulating it through the first endoscope; (c) measuring a concentration of the disinfectant agent in the sample of the second in-use disinfectant solution; (d) calculating actual concentration of the disinfectant agent in the concentrated disinfectant solution based upon the concentration of disinfectant agent in the sample of second in-use disinfectant solution; and (e) determining whether: (i) a volume of a third dose of concentrated disinfectant solution is increased compared to the volume of the second dose to make a third in-use disinfectant solution comprising the target concentration of disinfectant agent, or (ii) a volume of a third dose of concentrated disinfectant solution is about the same as the volume of the second dose to make a third in-use disinfectant solution comprising the target concentration of disinfectant agent.

Example 20

An automated apparatus for dynamic dosing of disinfectant solution in an endoscope reprocessing system, the apparatus comprising a control module that is operable to: (a) calculate a volume of an initial dose of concentrated disinfectant solution for dilution to make a first in-use disinfectant solution comprising a target concentration of disinfectant agent; (b) dilute the initial dose of concentrated disinfectant solution with diluting fluid to make the first in-use disinfectant solution comprising the target concentration of disinfectant agent; (c) apply the first in-use disinfectant solution to a first medical device; (d) measure a concentration of the disinfectant agent in the first in-use disinfectant solution after applying it to the first medical device; (e) calculate actual concentration of the disinfectant agent in the concentrated disinfectant solution based upon the concentration of disinfectant agent in the first in-use disinfectant solution after applying it to the medical device; and (f) determine whether: (i) a volume of a second dose of concentrated disinfectant solution is increased compared to the volume of the initial dose to make a second in-use disinfectant solution comprising the target concentration of disinfectant agent, or (ii) a volume of a second dose of concentrated disinfectant solution is about the same as the volume of the initial dose to make a second in-use disinfectant solution comprising the target concentration of disinfectant agent.

Example 21

The method according to any one or more of Examples 1 through 20, further comprising: (a) measuring a temperature of the first in-use disinfectant solution after applying it to the first medical device; (b) determining whether: (i) the temperature of the first in-use disinfectant solution is below an effective temperature for disinfection of the first medical device, or (ii) the temperature of the first in-use disinfectant solution is at or above an effective temperature for disinfection of the medical device; and (c) if the temperature of first in-use disinfectant solution is below the effective temperature for disinfection of the first medical device, increasing exposure time of the first medical device to the second in-use disinfectant solution.

V. Miscellaneous

While the teachings herein are provided in the context of disinfectant solutions, it should be understood that the same teachings may be readily applied in the context of sterilant solutions. In other words, the methods described herein may be readily used to dynamically adjust the dosage of sterilant into a sterilizing system, to account for degradation of the sterilant concentration.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method for dynamic dosing of disinfectant solution in a medical device reprocessing system, comprising:
   (a) calculating a volume of an initial dose of concentrated disinfectant solution for dilution to make a first in-use disinfectant solution comprising a target concentration of disinfectant agent;
   (b) diluting the initial dose of concentrated disinfectant solution with diluting fluid to make the first in-use disinfectant solution comprising the target concentration of disinfectant agent;
   (c) applying the first in-use disinfectant solution to a first medical device;
   (d) measuring a concentration of the disinfectant agent in the first in-use disinfectant solution after applying it to the first medical device;
   (e) calculating actual concentration of the disinfectant agent in the concentrated disinfectant solution based upon the concentration of disinfectant agent in the first in-use disinfectant solution after applying it to the medical device; and
   (f) determining whether:
      (i) a volume of a second dose of concentrated disinfectant solution is increased compared to the volume of the initial dose to make a second in-use disinfectant solution comprising the target concentration of disinfectant agent, or
      (ii) a volume of a second dose of concentrated disinfectant solution is about the same as the volume of the initial dose to make a second in-use disinfectant solution comprising the target concentration of disinfectant agent.

2. The method of claim 1, further comprising assuming that the disinfectant agent in the concentrated disinfectant solution is un-degraded when calculating the volume of an initial dose of concentrated disinfectant solution for dilution to make a first in-use disinfectant solution comprising a target concentration of disinfectant agent.

3. The method of claim 1, further comprising:
   (a) determining that the volume of the second dose of concentrated disinfectant solution is increased compared to the volume of the initial dose;
   (b) increasing the volume of the second dose compared to the volume of the initial dose; and
   (c) diluting the second dose with diluting fluid to make a second in-use disinfectant solution comprising the target concentration of disinfectant agent.

4. The method of claim 3, further comprising:
   (a) adding the diluting fluid into a basin configured to receive the medical device; and
   (b) dispensing the second dose into the diluting fluid in the basin.

5. The method of claim 4, further comprising dispensing the second dose into a pre-metering chamber.

6. The method of claim 4, further comprising:
   (a) measuring a temperature of first in-use disinfectant solution after applying it to the first medical device;
   (b) determining whether:
      (i) the temperature of the first in-use disinfectant solution is below an effective temperature for disinfection of the first medical device, or
      (ii) the temperature of the first in-use disinfectant solution is at or above an effective temperature for disinfection of the first medical device; and
   (c) if the temperature of first in-use disinfectant solution is below the effective temperature for disinfection of the first medical device, increasing exposure time of the first medical device to the second in-use disinfectant solution.

7. The method of claim 1, further comprising:
   (a) determining that the volume of the second dose of concentrated disinfectant solution is about the same as the volume of the initial dose to make a second in-use disinfectant solution comprising the target concentration of disinfectant agent; and
   (b) diluting the volume of the second dose of concentrated disinfectant solution with diluting fluid to make a second in-use disinfectant solution comprising the target concentration of disinfectant agent.

8. The method of claim 7, comprising:
   (a) adding the diluting fluid into a basin configured to receive the medical device; and
   (b) dispensing the second dose into the diluting fluid in the basin.

9. The method of claim 8, further comprising dispensing the second dose into a pre-metering chamber.

10. The method of claim 1, further comprising applying the second in-use disinfectant solution to a second endoscope.

11. The method of claim 1, further comprising:
(a) applying the second in-use disinfectant solution to a second medical device;
(b) measuring concentration of the disinfectant agent in the second in-use disinfectant solution after applying it to the second medical device;
(c) calculating actual concentration of the disinfectant agent in the concentrated disinfectant solution based upon the concentration of disinfectant agent in the second in-use disinfectant solution after applying it to the second medical device; and
(d) determining whether:
  (i) a volume of a third dose of concentrated disinfectant solution is increased compared to the volume of the second dose to make a third in-use disinfectant solution comprising the target concentration of disinfectant agent, or
  (ii) a volume of a third dose of concentrated disinfectant solution is about the same as the volume of the second dose to make a third in-use disinfectant solution comprising the target concentration of disinfectant agent.

12. The method of claim 1, further comprising calculating a degradation rate of the disinfectant agent and diluting an additional volume of the concentrated disinfectant solution with diluting fluid to make the first in-use disinfectant solution comprising the target concentration of disinfectant agent.

13. The method of claim 1, further comprising diluting an initial dose of concentrated disinfectant solution with dilution fluid to make an in-use disinfectant solution comprising a target concentration of disinfectant agents selected from: glutaraldehyde, hydrogen peroxide, ortho-phthalaldehyde, ozone, peracetic acid and combinations thereof.

14. The method of claim 13, further comprising diluting the initial dose of concentrated disinfectant solution with water to make an in-use disinfectant solution comprising a target concentration of ortho-phthalaldehyde of about 0.07 vol % or about 0.3 vol %.

15. The method of claim 13, further comprising diluting the initial dose of concentrated disinfectant solution with water to make an in-use disinfectant solution comprising a target concentration of peracetic acid of about 0.15 vol %.

16. A method for dynamic dosing of disinfectant solution in an endoscope reprocessing system, comprising automated steps of:
(a) calculating a volume of an initial dose of concentrated disinfectant solution for dilution to make a first in-use disinfectant solution comprising a target concentration of disinfectant agent;
(b) dispensing water into a basin configured to receive a first endoscope;
(c) dispensing the initial dose of concentrated disinfectant solution into the water to make the first in-use disinfectant solution comprising the target concentration of disinfectant agent;
(d) circulating the first in-use disinfectant solution from the basin through a first endoscope;
(e) collecting a sample of the first in-use disinfectant solution after circulating it through the first endoscope;
(f) measuring a concentration of the disinfectant agent in the sample of the first in-use disinfectant solution;
(g) calculating actual concentration of the disinfectant agent in the concentrated disinfectant solution based upon the concentration of disinfectant agent in the sample of first in-use disinfectant solution; and
(h) determining whether:
  (i) a volume of a second dose of concentrated disinfectant solution is increased compared to the volume of the initial dose to make a second in-use disinfectant solution comprising the target concentration of disinfectant agent, or
  (ii) a volume of a second dose of concentrated disinfectant solution is about the same as the volume of the initial dose to make a second in-use disinfectant solution comprising the target concentration of disinfectant agent.

17. The method of claim 16, further comprising:
(a) calculating a degradation rate of the disinfectant agent in the concentrated disinfectant solution;
(b) dispensing an additional volume of the concentrated disinfectant solution into the basin to account for degradation of the disinfectant agent; and
(c) diluting the initial dose and the additional volume of the concentrated disinfectant solution with the water in the basin to make the first in-use disinfectant solution comprising the target concentration of disinfectant agent.

18. The method of claim 16, further comprising:
(a) determining that the volume of the second dose of concentrated disinfectant solution is increased compared to the volume of the initial dose; and
(b) dispensing an increased volume of the second dose as compared to the volume of the initial dose of the concentrated disinfectant solution into the water in the basin to make a second in-use disinfectant solution.

19. The method of claim 18, further comprising:
(a) circulating the second in-use disinfectant solution from the basin through a second endoscope;
(b) collecting a sample of the second in-use disinfectant solution after circulating it through the first endoscope;
(c) measuring a concentration of the disinfectant agent in the sample of the second in-use disinfectant solution;
(d) calculating actual concentration of the disinfectant agent in the concentrated disinfectant solution based upon the concentration of disinfectant agent in the sample of second in-use disinfectant solution; and
(e) determining whether:
  (i) a volume of a third dose of concentrated disinfectant solution is increased compared to the volume of the second dose to make a third in-use disinfectant solution comprising the target concentration of disinfectant agent, or
  (ii) a volume of a third dose of concentrated disinfectant solution is about the same as the volume of the second dose to make a third in-use disinfectant solution comprising the target concentration of disinfectant agent.

* * * * *